US010835436B2

(12) United States Patent
Wiggermann

(10) Patent No.: US 10,835,436 B2
(45) Date of Patent: Nov. 17, 2020

(54) METHOD AND SYSTEM FOR ASSESSING COMPLIANCE WITH A PATIENT REPOSITIONING PROTOCOL

(71) Applicant: Hill-Rom Services, Inc., Batesville, IN (US)

(72) Inventor: Neal Wiggermann, Batesville, IN (US)

(73) Assignee: Hill-Rom Services, Inc., Batesville, IN (US)

(*) Notice: Subject to any disclaimer, the term of this patent is extended or adjusted under 35 U.S.C. 154(b) by 346 days.

(21) Appl. No.: 15/800,627

(22) Filed: Nov. 1, 2017

(65) Prior Publication Data

US 2019/0099310 A1    Apr. 4, 2019

Related U.S. Application Data

(60) Provisional application No. 62/567,951, filed on Oct. 4, 2017.

(51) Int. Cl.
| *A61G 7/10* | (2006.01) |
| *A61G 7/05* | (2006.01) |
| *A61G 7/015* | (2006.01) |
| *A61G 7/018* | (2006.01) |
| *A61G 7/057* | (2006.01) |
| *A61G 7/012* | (2006.01) |

(Continued)

(52) U.S. Cl.
CPC ........... *A61G 7/1065* (2013.01); *A61G 7/012* (2013.01); *A61G 7/015* (2013.01); *A61G 7/018* (2013.01); *A61G 7/0514* (2016.11); *A61G 7/0519* (2016.11); *A61G 7/0524* (2016.11); *A61G 7/0527* (2016.11); *A61G 7/05769* (2013.01); *A61G 7/108* (2013.01);

*A61G 7/1015* (2013.01); *A61G 7/1034* (2013.01); *A61G 7/1042* (2013.01); *A61G 7/1051* (2013.01); *A61G 7/1061* (2013.01); *G16H 20/30* (2018.01); *G16H 50/20* (2018.01); *A61B 5/1115* (2013.01); *A61G 10/00* (2013.01); *A61G 2203/44* (2013.01); *A61G 2205/60* (2013.01)

(58) Field of Classification Search
CPC .... G01G 19/445; A61G 7/0527; A61G 7/108; A61G 7/1015; A61G 7/1051; A61G 7/1061; A61G 2230/44
See application file for complete search history.

(56) References Cited

U.S. PATENT DOCUMENTS

| 6,133,837 A | 10/2000 | Riley | |
| 6,208,250 B1 * | 3/2001 | Dixon | .................. A61G 7/05 |
| | | | 340/539.12 |

(Continued)

*Primary Examiner* — Natalie Huls
(74) *Attorney, Agent, or Firm* — Barnes & Thornburg LLP

(57) ABSTRACT

A method for assessing compliance with a protocol requiring or advising the use of lift assist equipment for repositioning an occupant of an occupant support includes the steps of:
1) determining a measure of load borne by the occupant support over an interval of time;
2) determining how much the location of the occupant's center of mass relative to the occupant support has changed during the interval of time; and
3) assessing compliance with the protocol as a function of the load measure, the change of location, and a measure of the occupant's weight.

In one embodiment the load measure is an integral of load over an interval of time. An apparatus for carrying out the method comprises a processor and instructions which are executable by the processor.

37 Claims, 26 Drawing Sheets

(51) Int. Cl.
*G16H 50/20* (2018.01)
*G16H 20/30* (2018.01)
*A61B 5/11* (2006.01)
*A61G 10/00* (2006.01)

(56) References Cited

U.S. PATENT DOCUMENTS

| | | | |
|---|---|---|---|
| 7,253,366 B2 | 8/2007 | Bhai | |
| 7,437,787 B2 | 10/2008 | Bhai | |
| 10,543,137 B2* | 1/2020 | Hayes | G16H 40/40 |
| 2007/0174965 A1* | 8/2007 | Lemire | A61G 7/005 |
| | | | 5/600 |
| 2011/0046498 A1* | 2/2011 | Klap | A61B 5/0205 |
| | | | 600/534 |
| 2014/0013503 A1* | 1/2014 | Dixon | A61G 7/1073 |
| | | | 5/85.1 |
| 2014/0020175 A1 | 1/2014 | Dixon et al. | |
| 2014/0156222 A1* | 6/2014 | Roos | B60T 8/172 |
| | | | 702/175 |
| 2014/0259414 A1* | 9/2014 | Hayes | A61B 5/6892 |
| | | | 5/611 |
| 2016/0106345 A1 | 4/2016 | Kostic et al. | |
| 2016/0140307 A1* | 5/2016 | Brosnan | G16H 40/63 |
| | | | 600/324 |
| 2016/0213537 A1* | 7/2016 | Hayes | G06Q 50/22 |
| 2017/0020756 A1 | 1/2017 | Hillenbrand, II et al. | |

\* cited by examiner

METHOD AND SYSTEM FOR ASSESSING COMPLIANCE WITH A PATIENT REPOSITIONING PROTOCOL

CROSS REFERENCE TO RELATED APPLICATIONS

This application claims priority to U.S. Provisional Application 62/567,951 filed on Oct. 4, 2017, the contents of which are incorporated herein by reference.

TECHNICAL FIELD

The subject matter described herein relates to assessing whether or not a protocol for repositioning an occupant on an occupant support has been complied with. In one example application the occupant support is a hospital bed and the occupant is a patient.

BACKGROUND

Caregivers who work in health care facilities periodically need to reposition a patient from an initial position on a bed to a destination position on the bed. Repositioning can involve some degree of lifting including temporarily supporting a large portion of the patient's weight and moving the patient along the bed to the desired position. If done manually, i.e. without mechanical assistance, the act of repositioning the patient can cause injury to the caregiver due to the awkward posture the caregiver assumes, and asymmetric twisting of the caregiver's torso which exposes the spine to compression and shear forces that are known to increase the likelihood of back injury. In addition, to the extent that the caregiver slides the patient along the bed while the patient's weight is at least partially supported by the bed, the relative motion between the patient and the bed (mattress) can injure the patient's skin.

To mitigate the risk of caregiver and patient injury, a health care facility may advise or require that caregivers follow a protocol that specifies the use of lift equipment during patient repositioning. Such lift equipment typically includes a fabric sling and a hoist unit. In practice, and while the patient is on the bed, the caregiver maneuvers the sling and/or patient in order to position the sling underneath the patient. Once the patient is positioned on and secured in the sling, the hoist is used to lift the sling, and therefore the patient, until the bed no longer bears the patient's weight. Once the patient is hoisted off the bed, the hoist is used to move the patient laterally and/or longitudinally relative to the bed until the patient is suspended above the destination position. The hoist is then operated to lower the patient back onto the bed.

The above described protocol is effective at reducing caregiver injury. Because the patient is lifted, translated and then lowered, rather than being dragged across the bed, the protocol is also effective at reducing the likelihood of damage to the patient's skin. However these advantages accrue only if caregivers comply with the protocol. Because some caregivers fail to comply or comply only some of the time, it is valuable to assess whether or not compliance is occurring. If compliance or lack thereof can be attributed to specific caregivers, those caregivers can be commended or counseled as appropriate, thereby improving overall performance of the caregiving team. Statistics which show a high degree of overall compliance can also convince an insurer to reduce the cost of medical and disability insurance paid by the facility or its individual employees.

SUMMARY

A method for assessing compliance with a protocol requiring or advising the use of lift assist equipment for repositioning an occupant of an occupant support includes the steps of:
1) determining a measure of load borne by the occupant support over an interval of time;
2) determining how much the location of the occupant's center of mass relative to the occupant support has changed during the interval of time; and
3) assessing compliance with the protocol as a function of the load measure, the change of location, and a measure of the occupant's weight.

In one embodiment the load measure is an integral of load over an interval of time. An apparatus for carrying out the method comprises a processor and instructions which are executable by the processor.

BRIEF DESCRIPTION OF THE DRAWINGS

The foregoing and other features of the various embodiments of the method and apparatus described herein will become more apparent from the following detailed description and the accompanying drawings in which.

DETAILED DESCRIPTION

Figure 1:
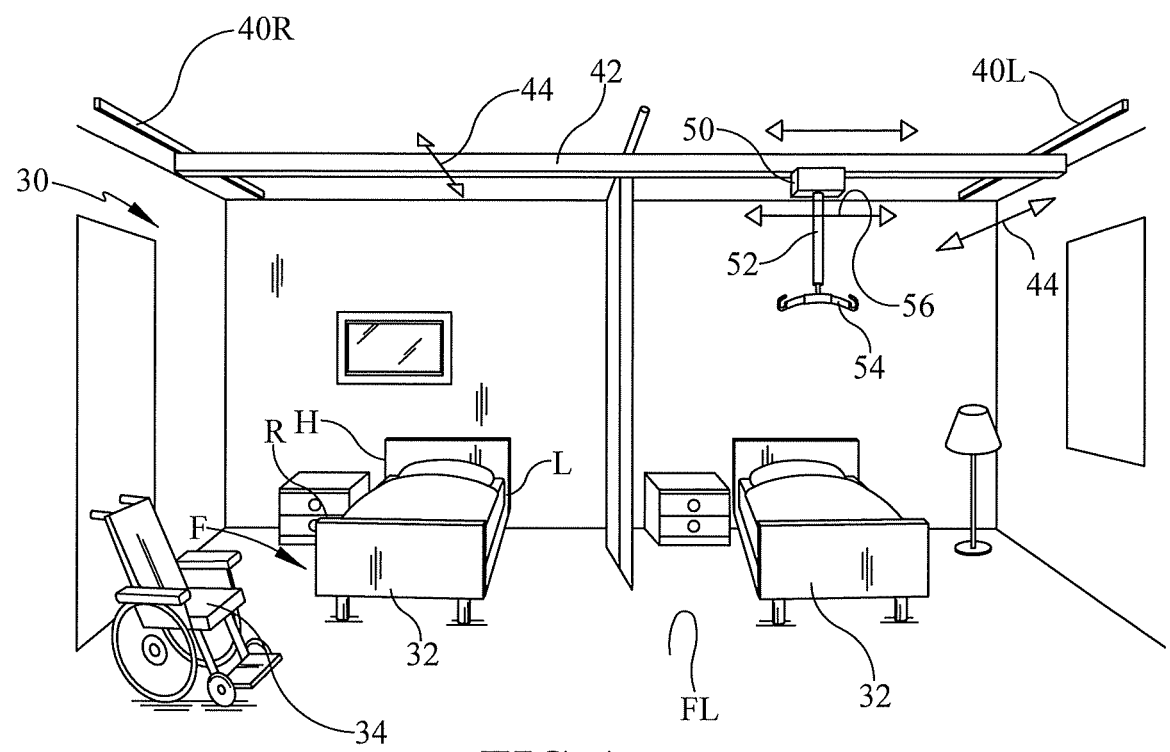
FIG. 1 is a view of a hospital room and selected components of a lift system.

Reference will now be made to embodiments of the invention, examples of which are illustrated in the accompanying drawings. Features similar to or the same as features already described may be identified by the same reference numerals already used. The terms "substantially" and "about" may be used herein to represent the inherent degree of uncertainty that may be attributed to any quantitative comparison, value, measurement or other representation. These terms are also used herein to represent the degree by which a quantitative representation may vary from a stated reference without resulting in a change in the basic function of the subject matter at issue.

Figure 2:
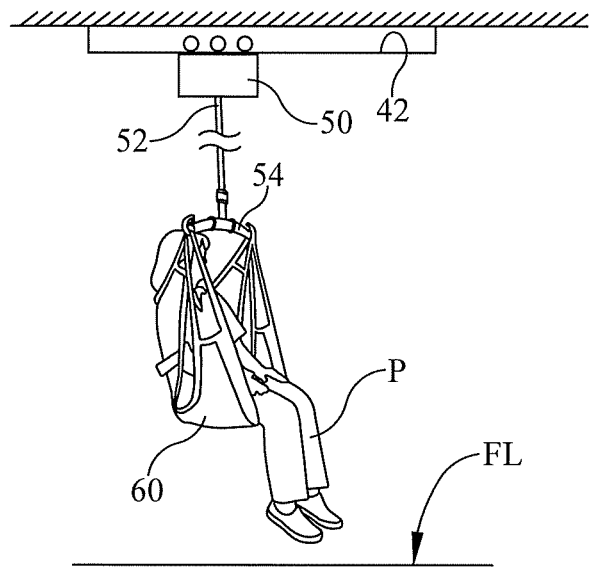
FIG. 2 is a view showing a sling component of the lift system and also showing a patient being supported by the lift system.

FIGS. 1-2 show a hospital room 30 a bed 32, a chair 34 and a patient lift system. The lift system includes a pair of ceiling mounted primary rails 40L, 40R and a traverse rail 42 movably mounted on the primary rails so that the traverse rail is translatable along the primary rails in forward and reverse longitudinal directions as indicated by double headed arrow 44. The lift system also includes a hoist 50 which houses a motor, not visible. The hoist includes a downwardly extending tether 52 and a slingbar 54 secured to the lower end of the tether. The hoist is mounted on the traverse rail so that the hoist is movable in laterally left and right directions as indicated by double headed arrow 56. The lift system also includes a sling 60 attached to left and right ends of the slingbar.

In operation a caregiver positions the sling under a patient, usually when the patient is on the bed or chair. (In this specification the patient may also be referred to an occupant, even at times when he or she is not actually occupying the bed.) The caregiver can then operate the motor to coil the tether into the housing thereby raising the sling and lifting the patient from the bed or chair. By pulling on the sling the caregiver can move the hoist laterally, i.e. along the traverse rail, and/or move the traverse rail longitudinally, i.e. along the primary rails, to move the patient laterally and/or longitudinally until the patient is suspended above a destination. The caregiver can then operate the motor to uncoil the tether and lower the patient to the destination. The lift system may be used to move the patient between any positions within the range of the primary and traverse rails, for example from the chair to a bed, or from one bed to the other. However the positions of interest in this application are an initial position and a destination position on the same bed or other occupant support.

Figure 3:
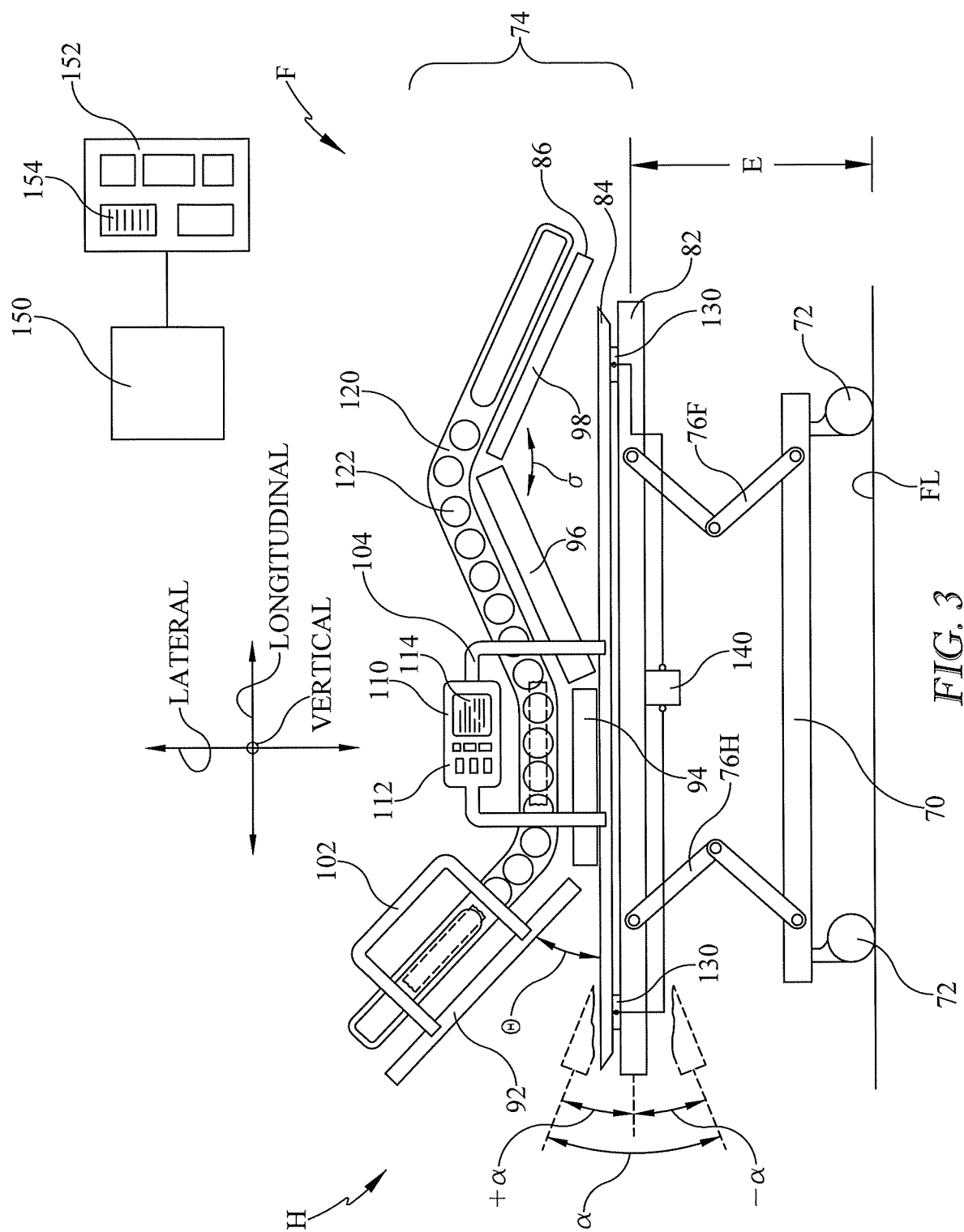
FIG. 3 is a schematic right side elevation view of a representative hospital bed which includes load cells.

FIG. 3 is a schematic view of a representative hospital bed. The bed extends longitudinally from a head end H to a foot end F and laterally from a left side L to a right side R. Left and right are taken from the perspective of a supine patient, hence the right side is the side visible in FIG. 3. The bed includes a base frame 70 supported on floor FL by casters 72, and an elevatable frame 74 supported on the base frame by a lift system that imparts elevation adjustability to the bed. In the illustration the lift system is represented by linkages 76F, 76H but typically includes other components such as actuators.

The elevatable frame includes a subframe 82, a weigh frame 84 supported on the subframe, and a deck 86 supported on the weigh frame. The illustrated deck is comprised of a torso or upper body section 92 for supporting a patient's torso, a seat section 94 for supporting the patient's buttocks, a thigh section 96 for supporting the patient's thighs and a calf section 98 for supporting the patient's calves and feet. As explained in more detail below some of the deck sections are orientation adjustable.

A set of head end siderails 102, one on the left side and one on the right, extend from deck torso section 92. A set of foot end siderails 104, one on the left side and one on the right, extend from elevatable frame 74. Only the right siderails are visible in FIG. 3. The siderails are positionable at a fully deployed or UP position (solid lines) and at a fully stowed or DOWN position (phantom lines showing a fragment of the uppermost portion of the siderail). The siderails may also be positionable at intermediate positions between the deployed and stowed positions.

The illustrated foot end siderail includes a user interface 110 with a keypad 112 and a video display 114. The keypad may be used to control various functions and features of the bed, including adjustments such as the elevation adjustment described above and other adjustments described below. The illustrated user interface is referred to as an outwardly facing user interface because it faces laterally outwardly or away from the patient. Therefore keypad 112 is readily accessible to caregivers, but not to the patient. The bed may also have an inwardly facing user interface that faces toward the patient. Typically the inwardly facing user interface controls fewer functions than the outwardly facing interface.

A mattress 120 rests atop the deck. At least part of the illustrated mattress comprises air bladders 122. The mattress is flexible enough to bend in response to changes of orientation of the orientation adjustable deck sections.

The representative bed also includes load cells 130, usually one at or near each corner of subframe 82. The load cells provide signals which indicate the weight of the weigh frame, siderails, deck, mattress, and any patient who happens to be occupying the bed. In general the load path from the weigh frame to the floor includes the load cells. Consequently, the load cells register the weight of the weigh frame itself and any other weight or load supported directly or indirectly by the weigh frame.

The bed also includes a patient position monitoring (PPM) system 140. The PPM system uses signals from the load cells to monitor the lateral and longitudinal coordinates of the patient's center of mass CM. The PPM can be used to determine patient's position on the bed and also to predict whether or not the patient has exited the bed or is attempting to do so. Example PPM systems and technologies are described in U.S. Pat. Nos. 6,208,250, 6,133,837, and 7,253,366.

The bed includes a number of adjustment systems for adjusting various features of the bed, thereby altering the physical state of the bed. As already noted, the bed includes a lift system for adjusting the elevation E of base frame 70 relative to floor FL. The lift system may also be used to adjust the orientation α of subframe 82 as indicated by the phantom subframe segments at the left side of the illustration.

The bed also includes a profile adjustment system for adjusting the profile of the deck, i.e. the orientation θ of torso section 92 and the angle σ defined by the thigh and calf sections 96, 98. The seat section 94 of the bed schematically illustrated in FIG. 3 is not orientation adjustable. As already noted mattress 120 bends to conform to the profile of the deck.

The bed also includes a mattress adjustment system for regulating the amount of air in bladders 122 and therefore the firmness of the mattress. The mattress can be made selectively firmer by introducing additional air into the bladders which increases air pressure inside the bladders. The mattress can be made softer by releasing or withdrawing air from the bladders which increases air pressure inside the bladders. The mattress may therefore be referred to as a condition adjustable mattress.

A caregiver or other user commands adjustments to elevation E, inclination angle α, profile angles θ and σ, and mattress condition (degree of firmness or softness) by way of user interface 110. A user command entered at interface keypad 112 triggers the operation of components (e.g. actuators) associated with one or more powered adjustment systems to effect the actual change in the physical state of the bed. The position of the siderails is adjusted manually. Nevertheless, this specification classifies the siderails as one of the adjustable systems of the bed.

FIG. 3 also shows a processor 150, and a memory 152 in communication with the processor. The contents of the memory include instructions 154 which are executable by the processor. The processor may be components of the bed, or one or both may be off-bed components.

Figure 4:
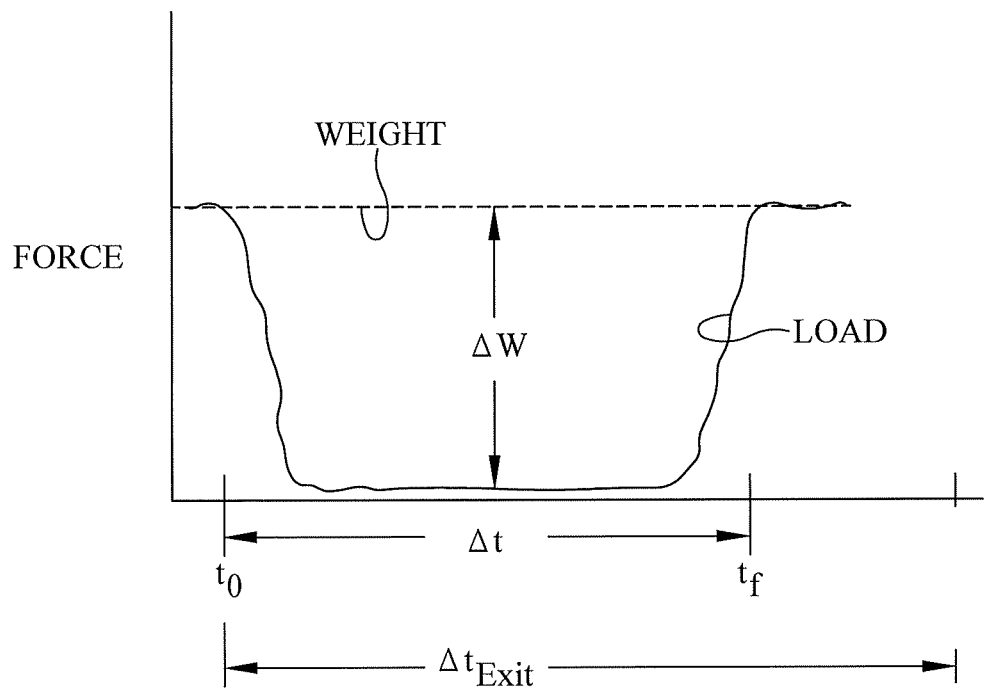
FIG. 4 is an illustrative graph showing force conveyed through the load cells of FIG. 3 vs. time for a compliant repositioning of a patient (solid lines) and also showing the patient's weight (dashed line).
Figure 5:
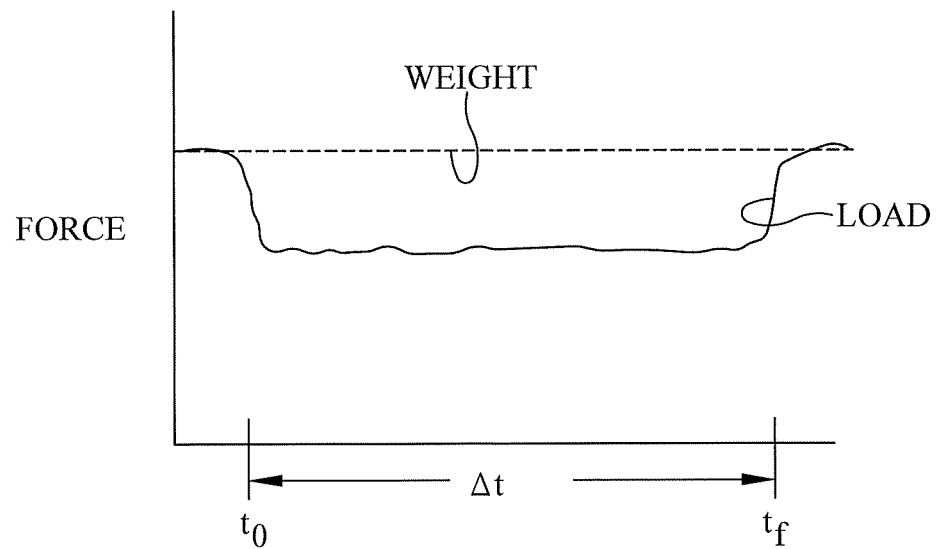
FIG. 5 is an illustrative graph showing force conveyed through the load cells of FIG. 3 vs. time for a noncompliant repositioning of a patient (solid lines) and also showing the patient's weight (dashed line).

FIGS. 4-5 are illustrative graphs showing force vs. time for a compliant repositioning of a patient (FIG. 4) and a noncompliant repositioning (FIG. 5). In both graphs a measure of the patient's weight is indicated by the dashed line and is constant during a time interval $\Delta t$ beginning at $t_0$ and ending at $t_f$. The weight of the patient may be determined in a number of ways, however one convenient way is to rely on a weight measuring system of the occupant support, for example the PPM system 140 which uses signals generated by load cells 130.

In one embodiment of the method the patient's weight is based on a discrete weight measurement carried out by the weight measuring system at a particular time. The determination of patient weight will disregard any forces which are sensed by the load cells but which do not represent patient weight. Nevertheless minor inaccuracies such as including the weight of sheets and blankets in the weight of the patient will not materially affect the various embodiments of the method described herein. The patient's weight measurement is stored in a memory and may be periodically updated. As a result of periodic updates, the graph of weight vs. time may exhibit some minor fluctuation over any given time interval that includes an update, including time interval $\Delta t$, but will nevertheless closely approximate the constant weight illustrated in FIGS. 4-5.

In a second embodiment the patient's weight is based on a historical record as determined by the weight measuring system, for example an average or median of the most recent load cell reading and several previous readings. The weight determination will disregard any forces which are sensed by the load cells but which do not represent patient weight. The most recently determined value of patient weight is stored in a memory and may be periodically updated. As a result of periodic updates, the graph of weight vs. time may exhibit some minor fluctuation over any given time interval that includes an update, including time interval $\Delta t$, but will nevertheless closely approximate the constant weight illustrated in FIGS. 4-5.

In both embodiments just described, although the load cells are a convenient and effective way to determine a measure of the patient's weight, it is not necessary to carry out the weight determination continuously or to update the stored value frequently.

In a third embodiment patient weight may be determined by a single measurement carried out on an external scale not associated with the bed. The weight measure may be entered into the memory by a caregiver using keypad 112 of user interface 110 or provided to the memory through a communication network linking the external scale and the memory.

In a fourth embodiment, the load cell signals may be taken as an indication of both load and weight, however if a large change takes place over a short time, the reading may be taken as an indication of only load, and the last reading prior to the change can be held in memory as the weight reading.

Continuing to refer to FIGS. 4-5, the solid line of each graph indicates a measure of the load exerted on the load cells 130 over a time interval beginning at initial time $t_0$ and ending at a later time $t_f$. The measure of load exerted on the load cells is also referred to herein as a measure of the load borne by the occupant support. The use of a continuous line to depict the load measure does not mean that the load measure must be an analogue signal. Discrete readings taken at a sample rate suitable for carrying out the method described herein are also satisfactory. In addition, the reader should appreciate that in practical embodiments values of load and weight may deviate from ideal values. For example the load cells may output a signal corresponding to a small load, or even a negative load, when a patient is not occupying the bed.

In FIG. 4, prior to $t_0$ the load is substantially equal to the patient's weight stored in memory. Starting at time $t_0$ the load diminishes to substantially zero indicating that the patient's weight was lifted off the bed. Time $t_0$ is the time at which the load begins to transition from a high value to zero or approximately zero. One way to identify $t_0$ is to continuously calculate the difference between a load reading at $t_n$ and an average of several previous readings ($t_{n-1}$, $t_{n-2}$, . . . ) readings, and assign $t_0$ to the time $t_{n-1}$, after which the difference exceeds a specified limit. At time $t_f$ the load value increases back to the value of the patient's weight. If, during the same time interval $\Delta t$, the patient's center of mass (CM) changed by more than a prescribed amount, it can be concluded that the patient underwent a repositioning and that the repositioning involved all or substantially all of the patient's weight being temporarily removed from the bed. This is consistent with the use of a lift to reposition the patient, and is therefore compliant with a protocol directing the use of lift equipment for patient repositioning.

In FIG. 5, prior to $t_0$ the load is also substantially equal to the patient's weight stored in memory. Starting at time $t_0$ the load diminishes to a value discernibly lower than the measure of weight, but significantly higher than zero, indicating that some but far less than all of the patient's weight was lifted off the bed. At time $t_f$ the load value increases back to the value of the patient's weight. If, during the same time interval $\Delta t$, the patient's center of mass CM changed by more than the prescribed amount, it can be concluded that the patient underwent a repositioning and that the repositioning involved less than all of the patient's weight being temporarily removed from the bed. This is consistent with a caregiver or caregivers bearing part of the patient's weight while dragging the patient from his initial location to a destination location and is therefore noncompliant with a protocol directing the use of lift equipment for patient repositioning.

Figure 6:
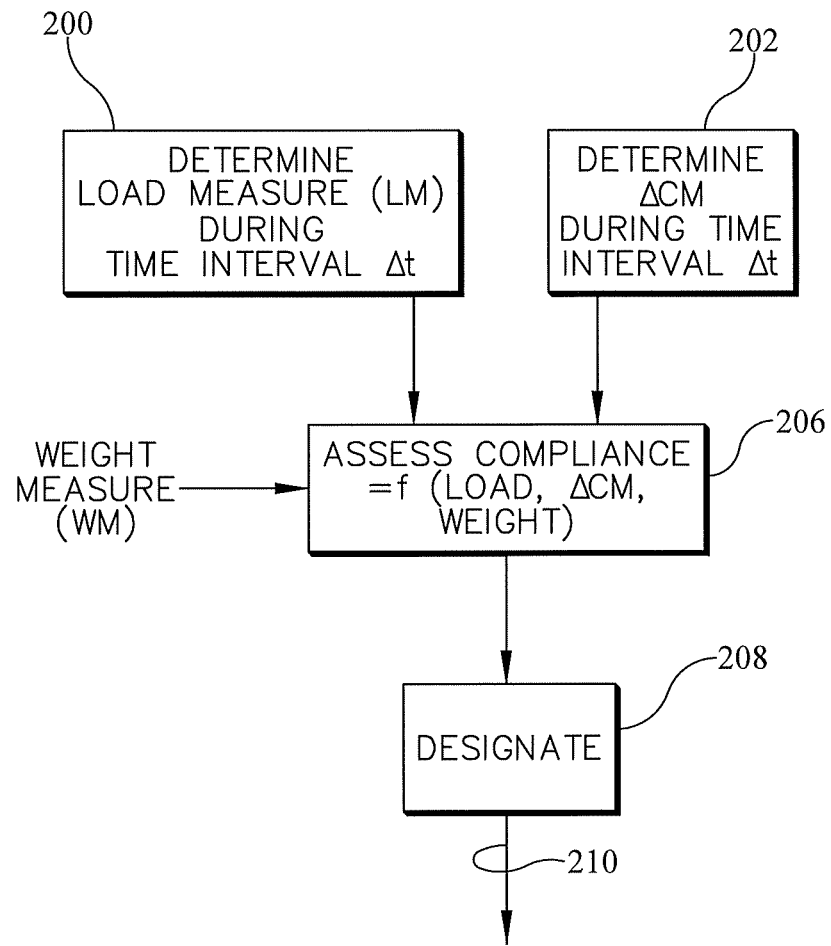
FIG. 6 is a block diagram of an embodiment of a method for assessing compliance with a protocol requirong the use of lift equipment when repositioning a patient on a bed.

FIG. 6 summarizes a method of assessing compliance with the protocol. At block 200 the method determines a load measure during time interval $\Delta t$. At block 202 the method determines how much the location of the patient's center of mass CM relative to the occupant support changed during the time interval, if at all. (In this specification the absence of a change of location of the patient's CM is considered to be a limit case of a nonzero change of location of the CM, and the symbol $\Delta$CM stands for the change in the location of the patient's center of mass relative to the bed, which may also be referred to more concisely as a change in the center of mass.) At block 206 the method assesses compliance with the protocol as a function of the load measure, the change of location and a measure of the patient's weight. At block 208 the method assigns a designation to the event associated with the load measure, the weight measure and the change of CM. The event may be designated to be a compliant event, a noncompliant event or an other than compliant event (not compliant, but also not necessarily noncompliant). Other designations may also be provided for. These include designating an event to be an exit event (patient exited the bed) or an exit precursor event (patient is in the bed but appears to be preparing to exit). In other block diagrams referred to in this specification, dedicated blocks may be used to distinguish between various outcomes. Path 210 shows the designation being conveyed to a destination such as display 114 or a database.

As is evident from FIGS. 4-5 the weight measure exhibits a temporal profile, albeit one which is the limit case of a substantially constant value. The load measure also exhibits a temporal profile which, during the time interval of the repositioning, is nonconstant. The method of assessing compliance or lack thereof accounts for the load profile and the weight profile.

The load measure may be the definite integral of the load versus time graph taken from $t_0$ to $t_f$, i.e. the area under the solid line curve from $t_0$ to $t_f$. Similarly, the weight measure may be the definite integral of the weight versus time graph taken from $t_0$ to $t_f$, i.e. the area under the broken line curve from $t_0$ to $t_f$. The step of assessing compliance with the protocol then involves comparing the values of those integrals, taking into account any change in the patient's CM.

Because it is not necessary to measure weight continuously a real time weight versus time signal may not be available for integration. Accordingly, the weight integral may be represented by or estimated from a surrogate which is based on the non-real time weight stored in memory. For example, if the weight stored in memory is 75 kilograms and time interval $\Delta t$ is 12 seconds, then the product 12×75=900 could be the surrogate of the actual integration. The surrogate takes the place of an integration based on real time information.

Figure 7:
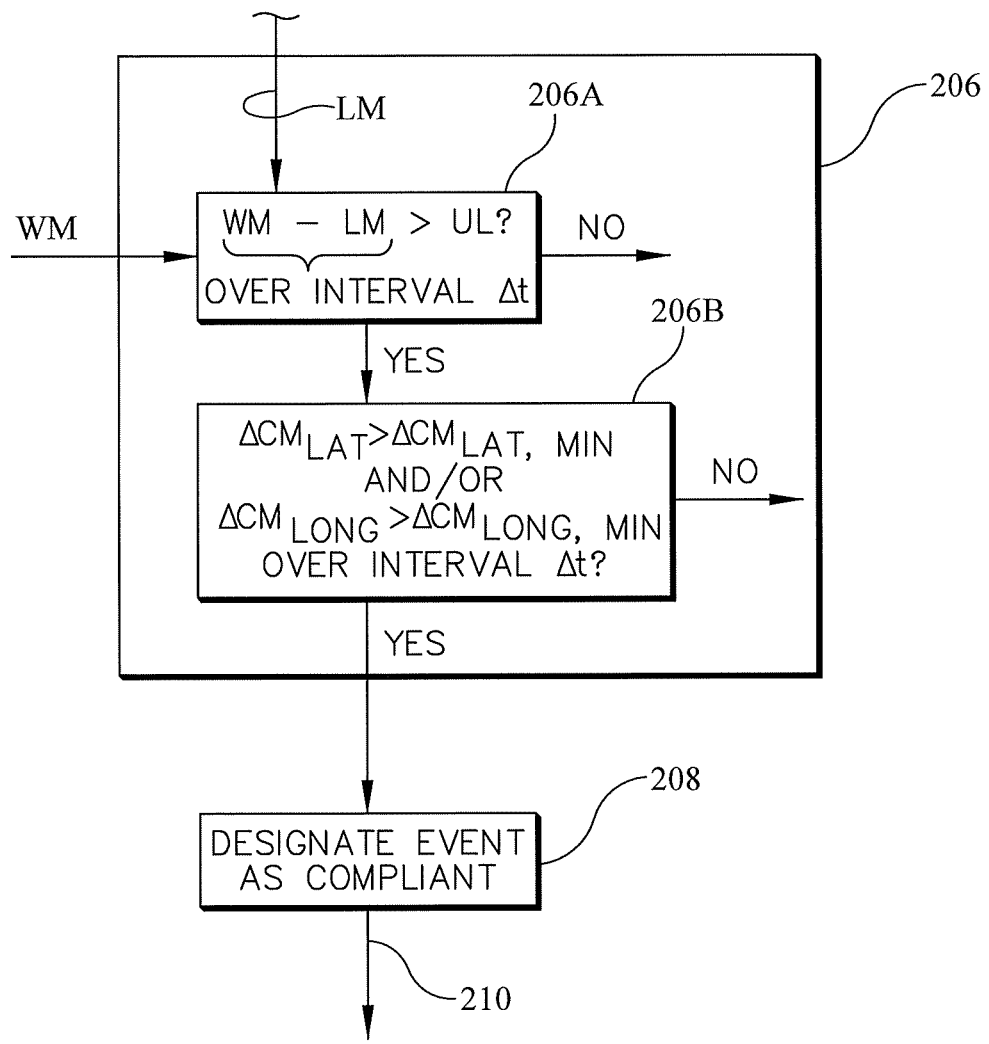
FIG. 7 is a partial block diagram showing further details of one of the blocks of FIG. 6.

FIG. 7 is a partial block diagram showing further details of block 206. At block 206A the method subtracts the value of the load measure LM over interval $\Delta t$ from the value of the weight measure WM and determines if the load measure deviates from the weight measure by more than an upper limit UL. If so the method proceeds to block 206B where it determines if the change of the patient's center of mass in the lateral direction $\Delta CM_{LAT}$ or the change of the patient's center of mass in the longitudinal direction $\Delta CM_{LONG}$ (or both) have changed by respective minimum amounts $\Delta CM_{LAT, MIN}$, $\Delta CM_{LONG, MIN}$ during interval $\Delta t$. The requirement for the change in CM to exceed minimum amounts guards against the possibility that lifting the patient's weight off the bed and subsequently reapplying it at substantially the same location will be identified as a compliant event. However the test of block 206B can be omitted if it is decided (e.g by a system designer) that lifting the patient's weight off the bed and subsequently reapplying it at substantially the same location should qualify as a compliant event, although such an event would not qualify as a repositioning event in the sense of moving the patient's CM from one location on the bed to another. One or both of $\Delta CM_{LAT, MIN}$, $\Delta CM_{LONG, MIN}$ can be zero if desired.

Figure 8:
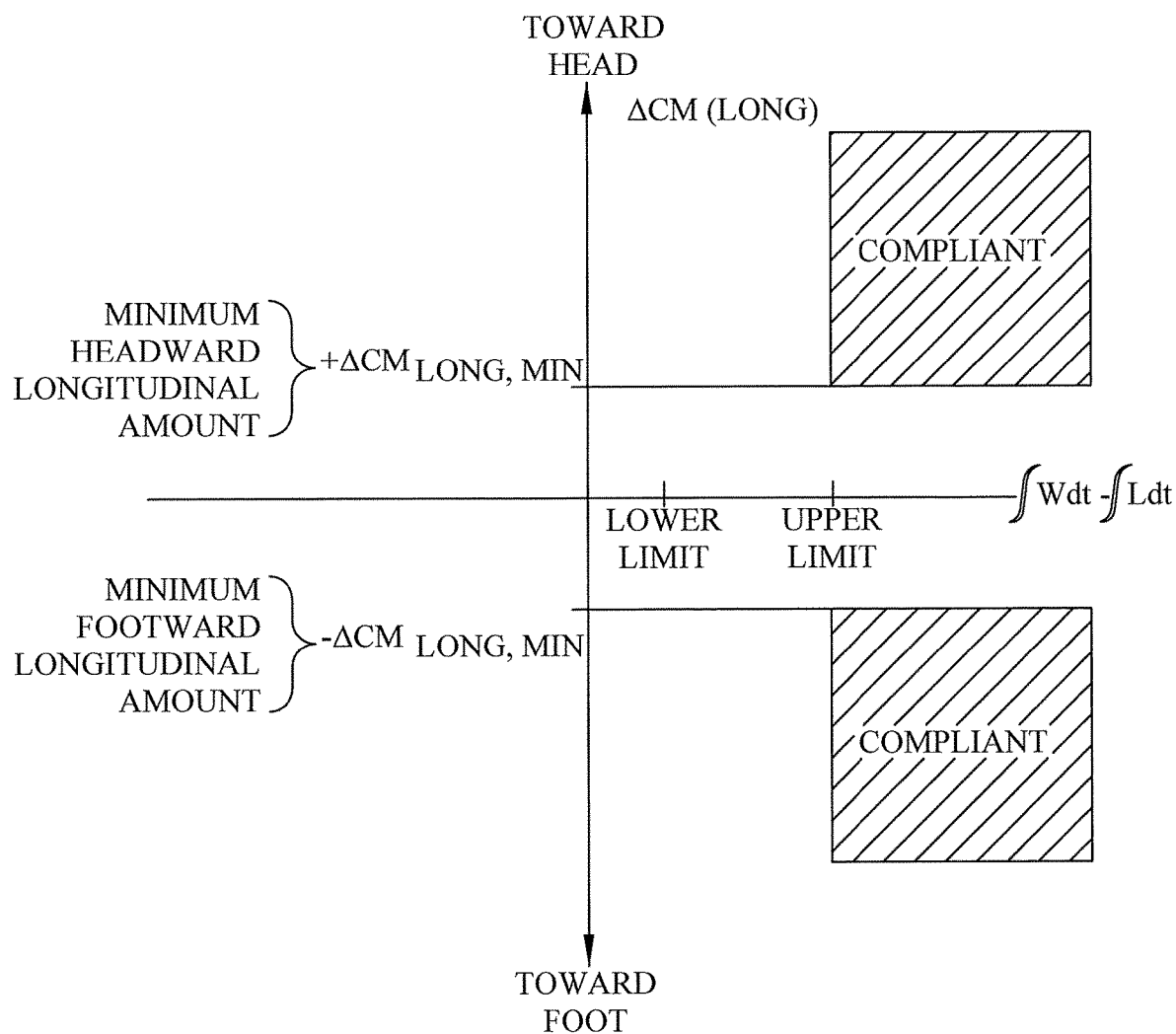
FIG. 8 is a chart depicting the logic of FIG. 7 in a more graphical form for the specific case of a purely longitudinal change in the patient's center of mass and in which a measure of the patient's weight and a measure of the load conveyed through the load cells of FIG. 3 are both represented by integrals of force over an interval of time and in which the event under consideration qualifies as a compliant patient repositioning.

FIG. 8 is an example depicting the logic of FIG. 7 in a more graphical form for the specific case of a purely longitudinal change in the center of mass and in which the weight measure and load measure are the integrals described above. The horizontal axis is the difference in the integrals. The vertical axis is the longitudinal change in the center of mass. The crosshatched areas are regions of compliance. If $\Delta CM_{LONG, MIN}$ were zero as described above, the regions of compliance would join each other at the horizontal axis. A graph accounting for a purely lateral change in the patient's center of mass would have a similar appearance. In general both lateral and longitudinal displacements may be accounted for.

If the order of terms in the subtraction at block 206A of FIG. 7 were reversed from WM-LM to LM-WM, it would be necessary to change the "greater than an upper limit" condition to "less than a lower limit". Alternatively the absolute value of LM-WM could be used without changing "greater than an upper limit" to "less than a lower limit". These variants are algebraically equivalent to each other. Accordingly, algebraic statements in this specification, including the claims, include their algebraic equivalents. In addition, this specification uses words and phrases such as "less than", "greater than", "prior to", "before", and "after" to compare quantities, including time. It is evident that an equality condition can be paired with the foregoing expressions without affecting the principles of the method. Accordingly, the specification and claims encompass both inclusion and exclusion of the equality condition. It is similarly evident that if a quantity can be either on one side of a threshold, or equal to or on the other side of the threshold, the equality condition can be paired with either the one side or the other side (but logically not both) without affecting the principles of the method. Accordingly, the specification and claims encompass inclusion of the equality condition with either side of a threshold expression, but not both. For example, the operator pair (>, <) encompasses (>, ≤) and (≥, <). Similarly, (≥, <) encompasses (>, ≤) and (≥, <).

Figure 9:
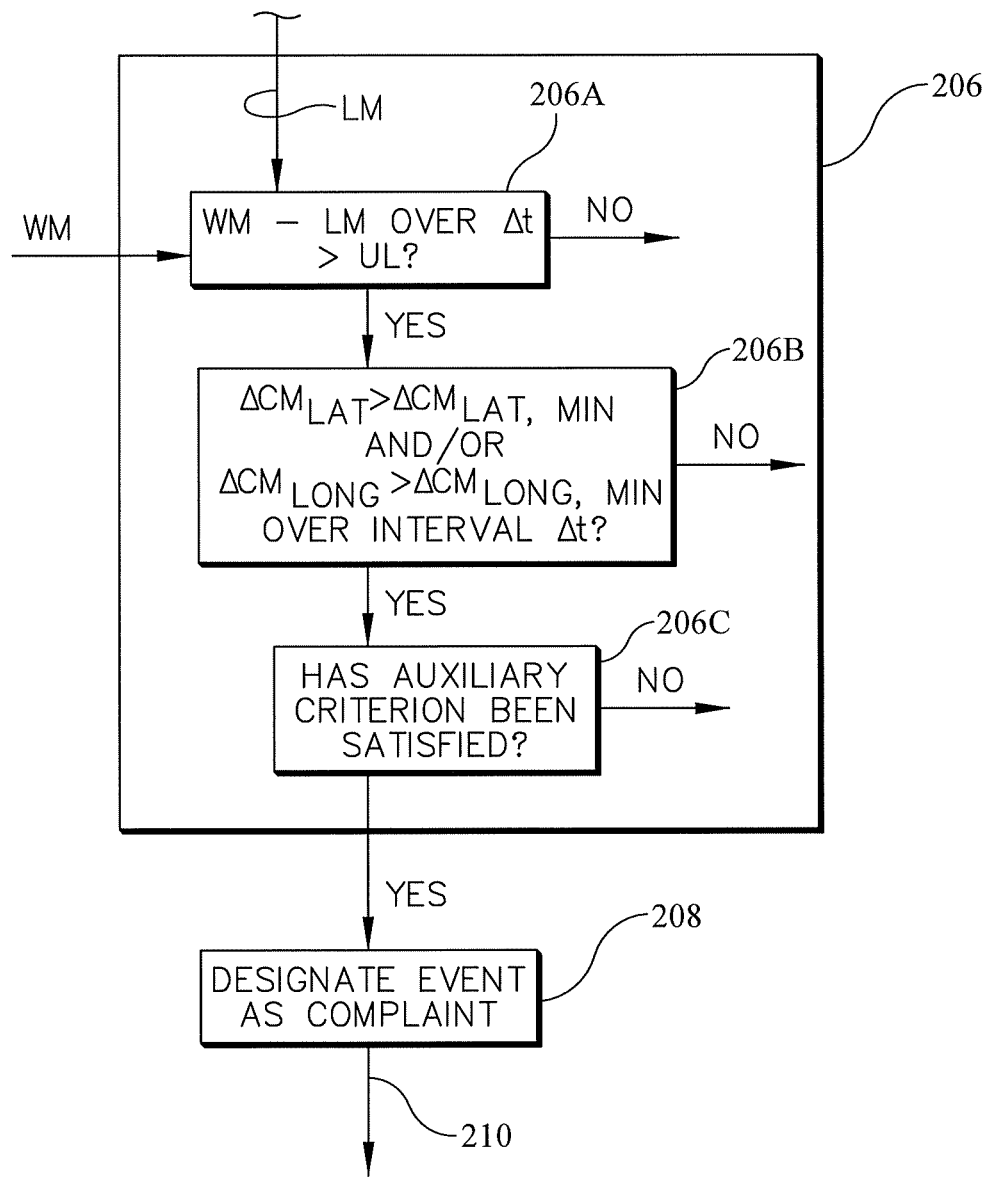
FIG. 9 is a block diagram similar to that of FIG. 7 in which designating the change of patient location as a compliant event is further conditioned on satisfaction of at least one auxiliary criterion.

FIG. 9 is a block diagram similar to that of FIG. 7 in which designating the change of location as a compliant event is further conditioned on satisfaction of at least one auxiliary criterion at block 206C. In the diagram, an event which satisfies the tests at blocks 206A and 206B is a candidate event. If, at block 206C, the method determines that the auxiliary criterion has been satisfied, the method proceeds to block 208 and designates the candidate event as a compliant event.

Figure 10:
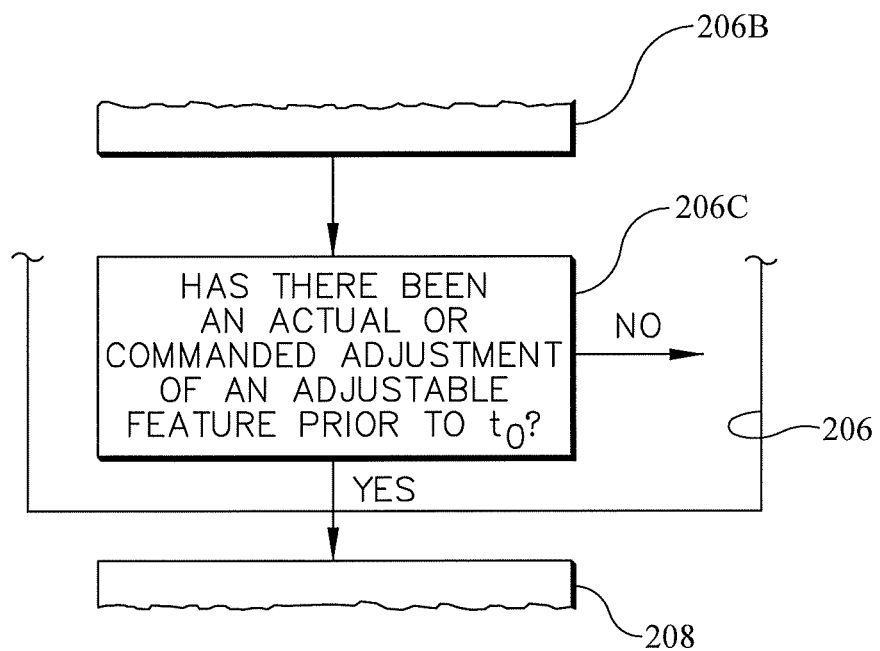
FIGS. 10-17, are a views of one of the blocks of FIG. 9 each showing one example of an auxiliary criterion.

Referring to FIG. 10, one example of an auxiliary criterion is an actual or commanded adjustment of an adjustable feature of the bed prior to $t_0$, i.e. prior to the occurrence of the candidate event. Examples include actual or commanded adjustment of 1) orientation angle α, 2) profile as represented by angles θ and/or σ, 3) elevation E, 4) siderail status (e.g. deployed, stowed or somewhere in between) and 5) firmness condition of the mattress.

Whether or not an actual adjustment has taken place (which may include the adjustment being underway but not yet completed) may be determined by monitoring sensors which indicate that the adjustment has taken place or is underway. One example is a feedback sensor indicating the length of a variable length actuator. Whether or not an adjustment has been commanded (but has not yet progressed enough to be discernible from feedback sensors), can be determined from signals generated when a user uses a key on keypad 112 which commands the adjustment to occur.

Figure 11:
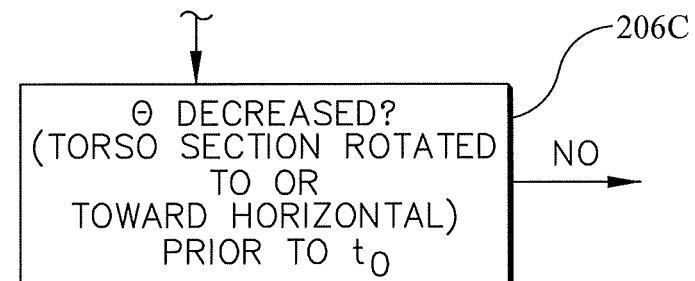
Figure 12:
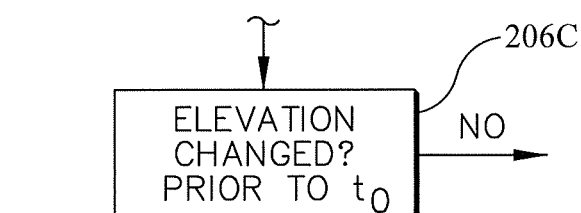
Figure 13:
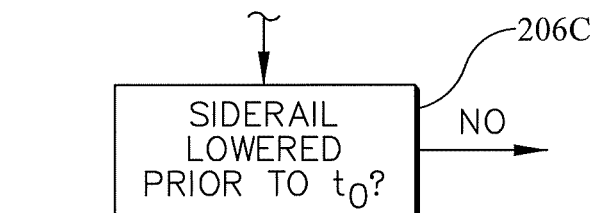

Referring to FIGS. 11-13, more specific examples of auxiliary conditions to be satisfied may include an actual adjustment prior $t_0$ to that would be expected to preceed a compliant repositioning event or a command to effect that adjustment. Examples include:

1) changing torso angle θ so that torso section 92 rotates toward a horizontal orientation (FIG. 11),
2) changing elevation E to an elevation consistent with a caregiver providing assistance to position a sling under the patient. In particular a change in elevation from its minimum value (the elevation frequently used when a caregiver is not present) to a higher elevation may be especially suggestive of a precursor to a compliant repositioning event because the caregiver would likely make that elevation change to make it easier to position the sling underneath the patient, (FIG. 12) and
3) lowering a siderail, which is another action consistent with a caregiver providing assistance to position a sling under the patient (FIG. 13).

Figure 14:
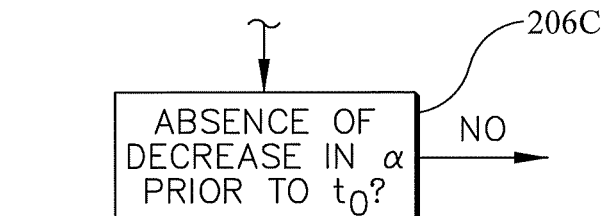
Figure 15:
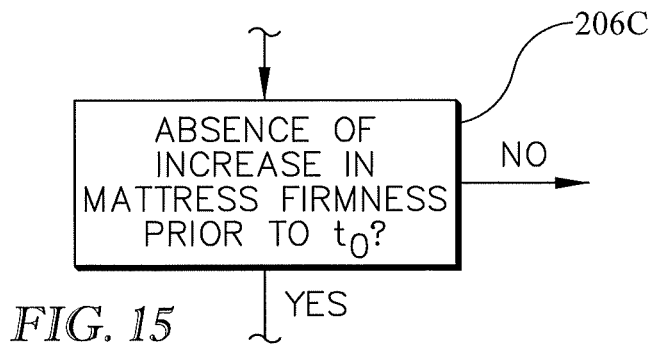

Referring to FIGS. 14-15 more specific examples of auxiliary conditions to be satisfied may also include the absence of an actual adjustment prior $t_0$ to that would be expected to preceed a noncompliant repositioning event or the absence of a command to effect that adjustment. Examples of conditions that may be expected to preceed a noncompliant event include:

1) referring momentarily to FIG. 3, changing orientation angle α from a less head down orientation to a more head down orientation (from a positive value to a less positive value, from a positive value to a negative value, or from a negative value to a more negative value) (FIG. 14), and
2) placing the mattress in a condition more favorable than not for manual repositioning, for example increasing the firmness of the mattress, particularly to its maximum firmness, or increasing the air pressure inside the bladder (FIG. 15).

Figure 16:
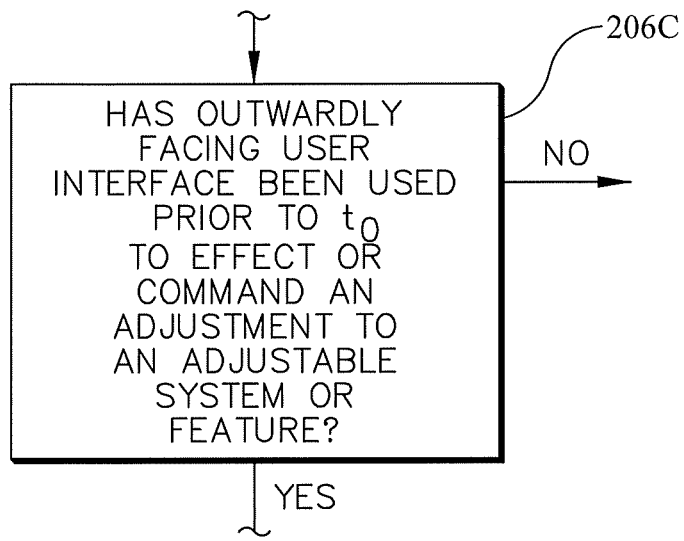

Referring to FIG. 16 another possible auxiliary criterion to be satisfied in order to designate an event as a compliant repositioning event is the use of an outwardly facing keypad (e.g. keypad 112 of FIG. 3) prior to $t_0$ to effect an adjustment or to command an adjustment to one of the adjustable systems. The outwardly facing keypad, rather than an inwardly facing keypad, is the one most likely to be used by a caregiver to command a pre-repositioning adjustment.

Figure 17:
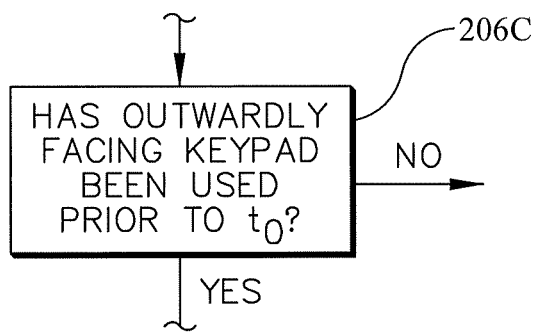

Referring to FIG. 17, another possible auxiliary criterion to be satisfied in order to designate an event as a compliant repositioning event is the use of an outwardly facing keypad prior to $t_0$. The criterion of FIG. 17, unlike that of FIG. 16, does not constrain the purpose for which the keypad was used.

In a further variant of the method, when the auxiliary criterion involves the performance of an action, such as an adjustment of an adjustable system, issuance of a command to do so, or use of a keypad, the criterion is recognized as having been satisfied only if the action occurred no more than a specified amount of time before $t_0$. Use of such a time limit helps to ensure that the action under consideration is related to the event under consideration.

The auxiliary criteria of FIGS. 11-15 and 17 have been presented individually. However two or more auxiliary criteria could be used, in which case the method would branch to block 208 if Boolean tests applied to those criteria (e.g. AND, OR, NAND, NOR, XOR) were satisfied. FIG. 16 is an example in which two criteria (an actual or commanded adjustment and use of an outwardly facing user interface to effect the adjustment or issue the command) are AND'd together.

Figure 18:
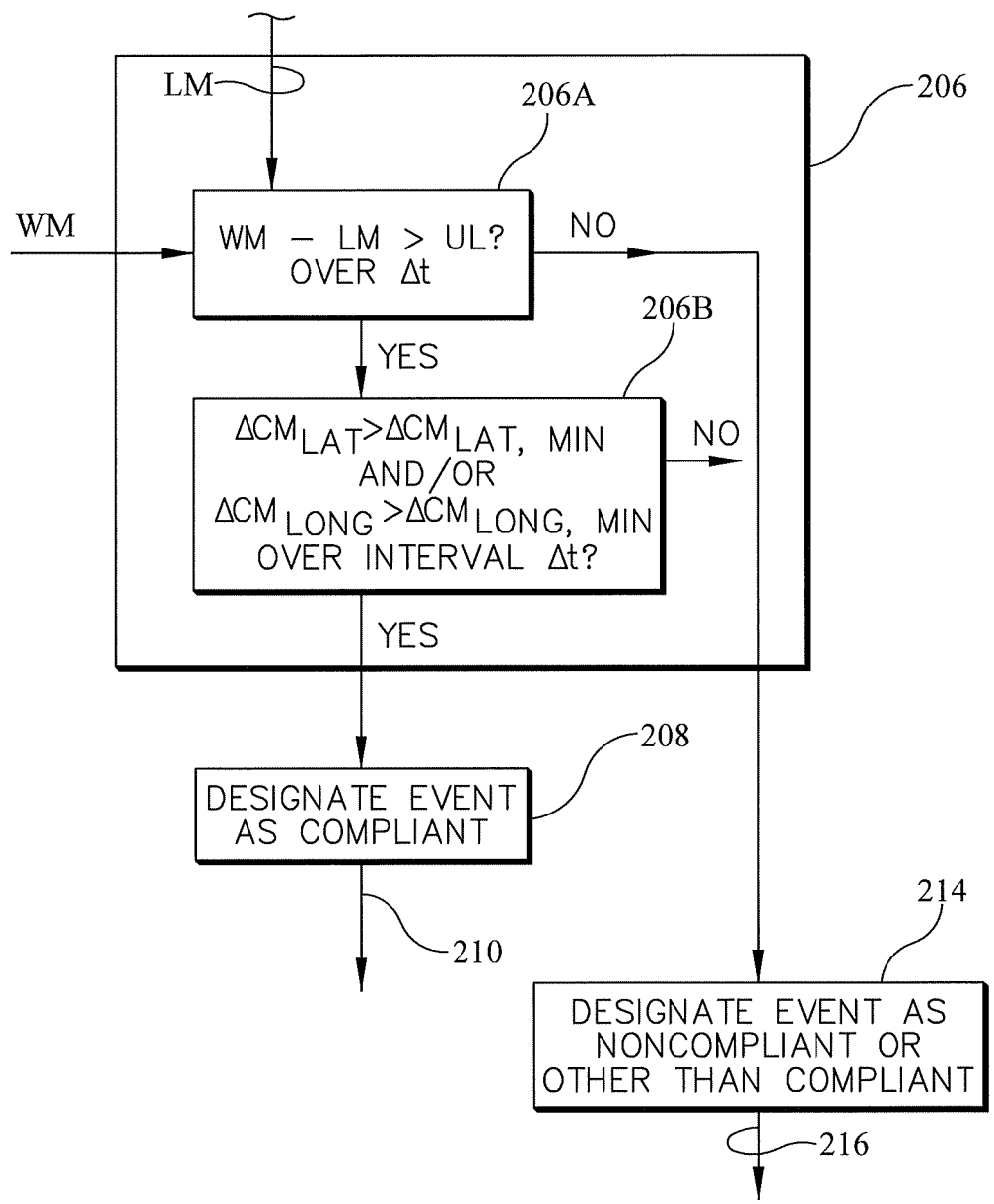
FIG. 18 is a block diagram similar to that of FIG. 7 including a block which designates an event as noncompliant.
Figure 19:
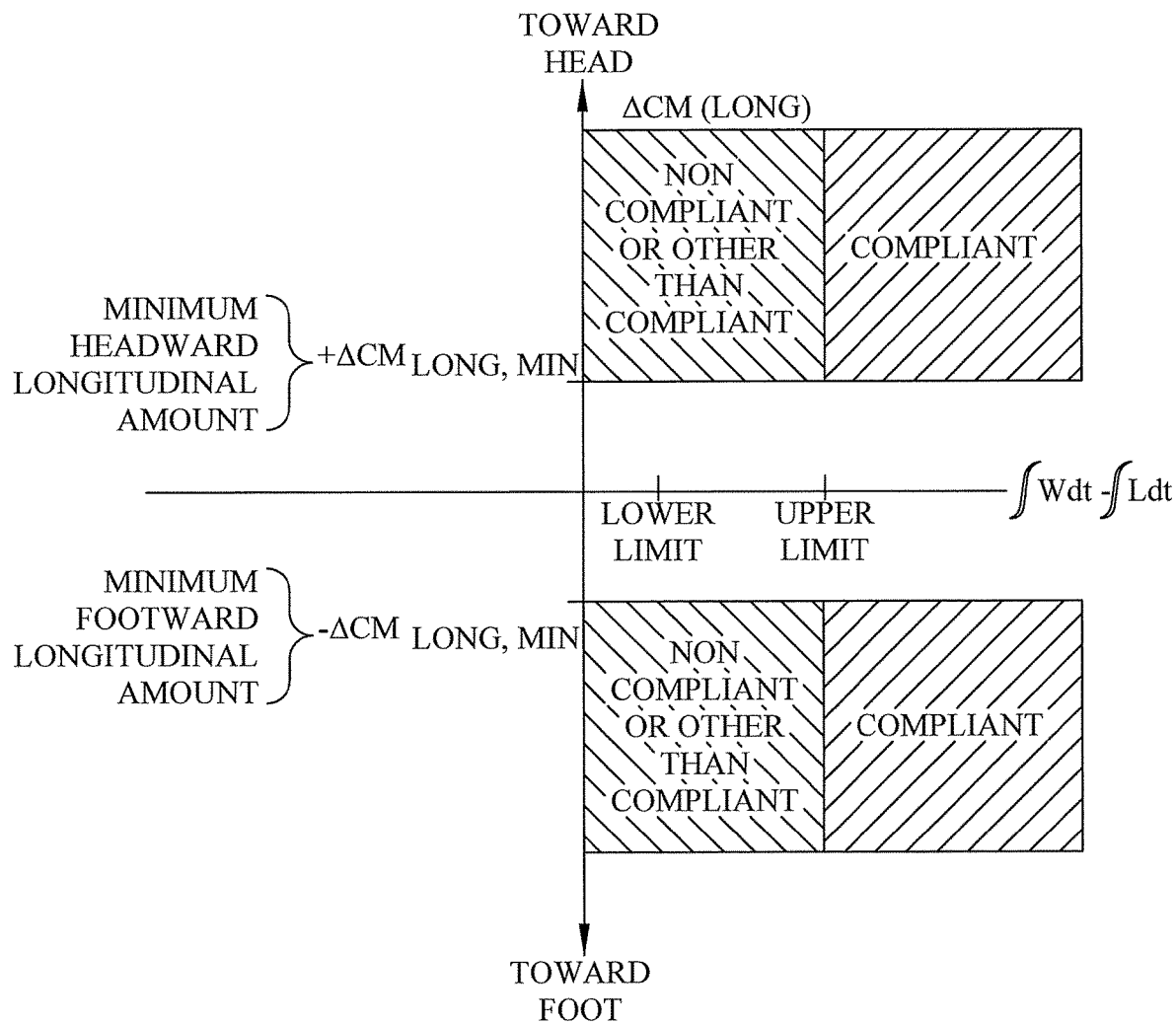
FIG. 19, is a chart similar to that of 8 with negatively sloped crosshatching showing a region which may be designated as noncompliant or other than compliant.

FIG. 18, is a block diagram similar to that of FIG. 7. If, at block 206A, it is determined that WM−LM is not greater than the upper limit UL, the method follows the "NO" branch to block 214 and designates the event as a noncompliant event or as an other than compliant event (not compliant, but also not necessarily noncompliant). Path 216 shows the designation being conveyed to a destination such as display 114 or a database. FIG. 19 is a chart similar to that of FIG. 8 with the noncompliant or other than compliant region shown with negatively sloped crosshatching. A graph accounting for a purely lateral change in the patient's center of mass would have a similar appearance. In general both lateral and longitudinal displacements may be accounted for.

Figure 20:
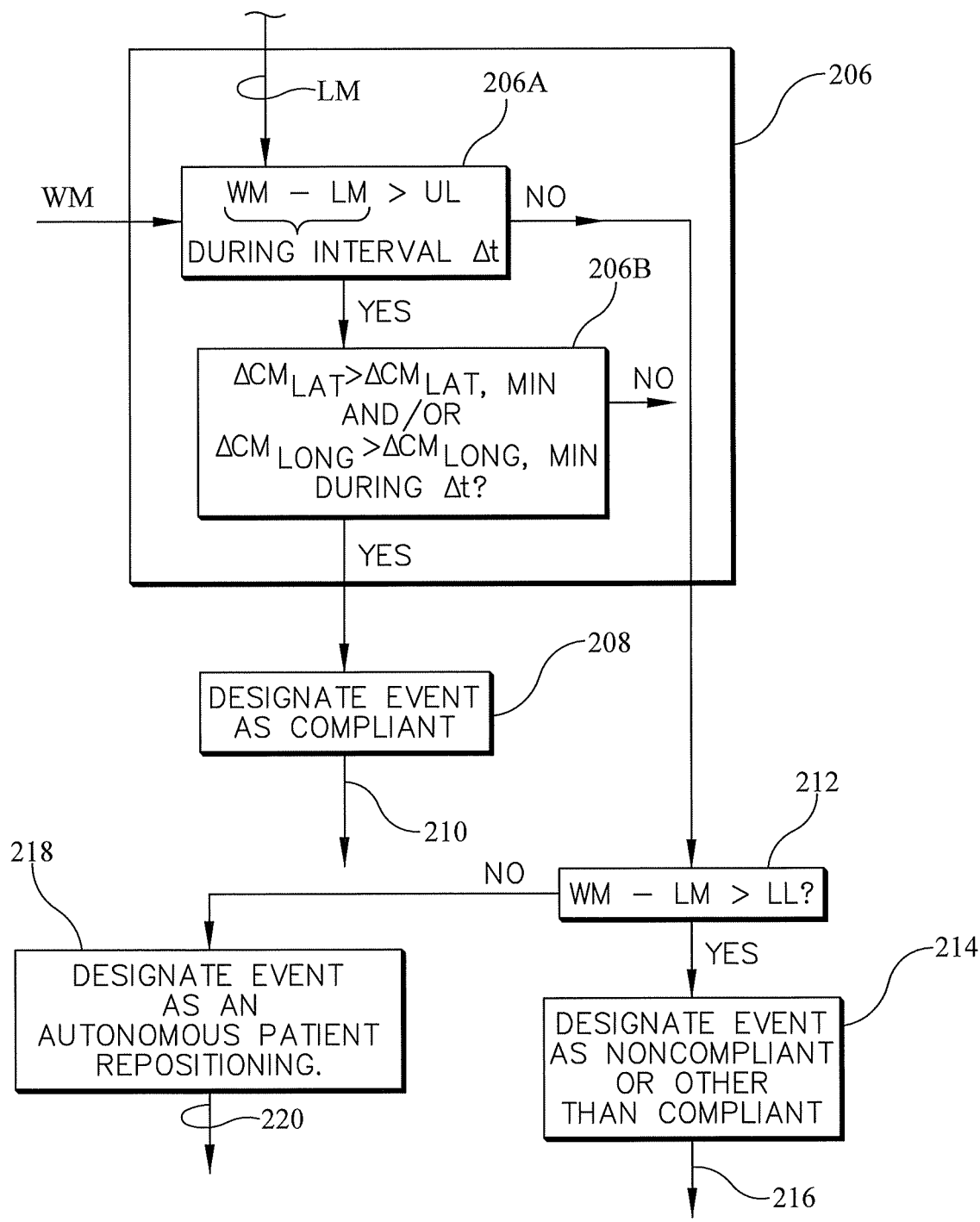
FIG. 20 is a block diagram similar to that of FIG. 18, showing a variant of the method in which designating the change of location to be a noncompliant event or an other than compliant event is further conditioned on the load measure deviating from the weight measure by more than a lower limit LL which is less than the upper limit UL.

FIG. 20 is a block diagram similar to that of FIG. 18, showing a variant of the method in which designating the change of location to be a noncompliant event or an other than compliant event is further conditioned on the load measure deviating from the weight measure by more than a lower limit LL which is less than the upper limit UL. The method carries out the test at block 212. If the test is satisfied the method proceeds to block 214 where it designates the event as a noncompliant event or as an other than compliant event. Path 216 shows the designation being conveyed to a destination such as display 114 or a database.

Figure 21:
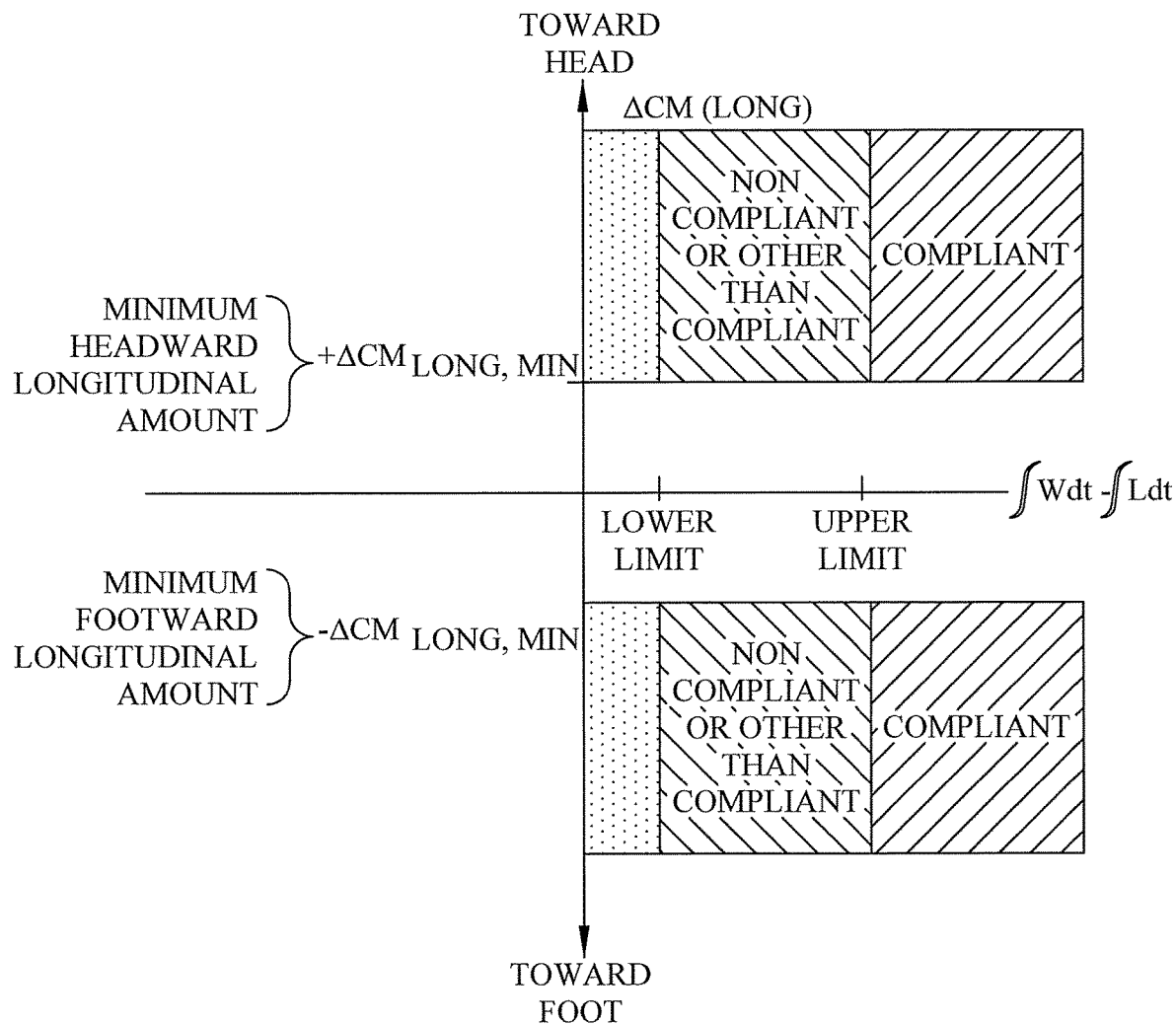
FIG. 21 is a chart similar to that of FIG. 19 in which the region designated as noncompliant or other than compliant does not extend to the left of the lower limit of FIG. 20.

FIG. 20 also illustrates that if the test at block 212 reveals that WM-LM is less than the lower limit, the method may branch to block 218 and report that the event is an autonomous patient repositioning (i.e. the patient repositioned himself). Path 220 shows the designation being conveyed to a destination such as display 114 or a database. FIG. 21 is a chart similar to that of FIG. 19 with the noncompliant region bounded by the upper and lower limits. The stippled regions to the left of the lower limit are regions corresponding to the autonomous repositioning of block 218 of FIG. 20. A graph accounting for a purely lateral change in the patient's center of mass would have a similar appearance. In general both lateral and longitudinal displacements may be accounted for.

Continuing to refer to FIG. 20, in theory an autonomous repositioning will correspond to the weight integral minus the load integral having a value of zero. This is because any positive load fluctuations (load greater than weight as a result of the patient jostling against the mattress) will balance out any negative load fluctuations (load less than weight as a result of the patient jostling against the mattress). However in practice a perfect balance may not occur, thereby giving rise to a value in the stippled region of FIG. 21. Indeed, the stippled region may extend to the left of the vertical axis.

Figure 22:
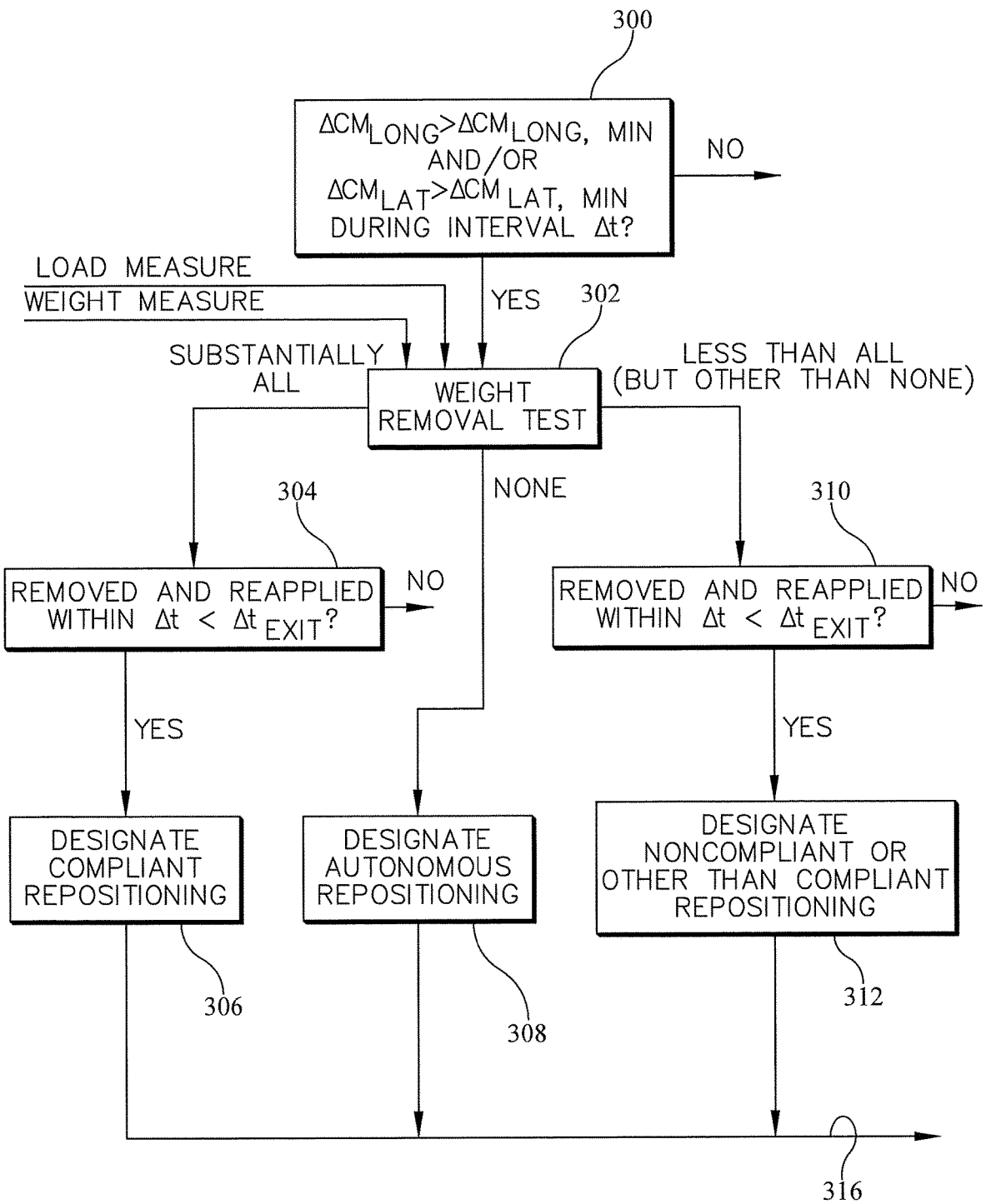
FIG. 22 is a block diagram of a time dependent embodiment of the method.

FIGS. 4, 5 and 22 illustrate another embodiment embodiment. At block 300 the method determines if the change of the patient's center of mass in the lateral direction $\Delta CM_{LAT}$ or the change of the patient's center of mass in the longitudinal direction $\Delta CM_{LONG}$ (or both) have changed by respective minimum amounts $\Delta CM_{LAT, MIN}$, $\Delta CM_{LONG, MIN}$. If so the method proceeds to block 302 where it carries out a weight removal test based on the load measure and weight measure. If the outcome of the test at block 302 reveals that all or substantially all of the patient's weight was removed, e.g. as seen on FIG. 4, the method proceeds to block 304 where it determines if time interval $\Delta t$, the difference between $t_0$ and $t_f$, is less than a value, $\Delta t_{EXIT}$ where $\Delta t_{EXIT}$ is an exit time threshold long enough to suggest that the patient has exited from the bed. If so, the method proceeds to block 306 and designates the event a compliant patient repositioning.

If the outcome of the test at block 302 reveals that none or essentially none of the patient's weight was removed from the bed, the method proceeds to block 308 where it designates the event as an autonomous patient repositioning.

If the outcome of the test at block 302 reveals that less than all (but other than none or essentially none) of the patient's weight was removed, e.g. as seen on FIG. 5, the method proceeds to block 310 where it determines if time interval $\Delta t$, the difference between $t_0$ and $t_f$, is less than the value $\Delta t_{EXIT}$. If so, the method proceeds to block 312 and designates the event as noncompliant or other than compliant. In an alternative variant block 310 is not present, and the method proceeds directly to block 312. Path 316 shows the designation being conveyed to a destination such as display 114 or a database.

Figure 23:
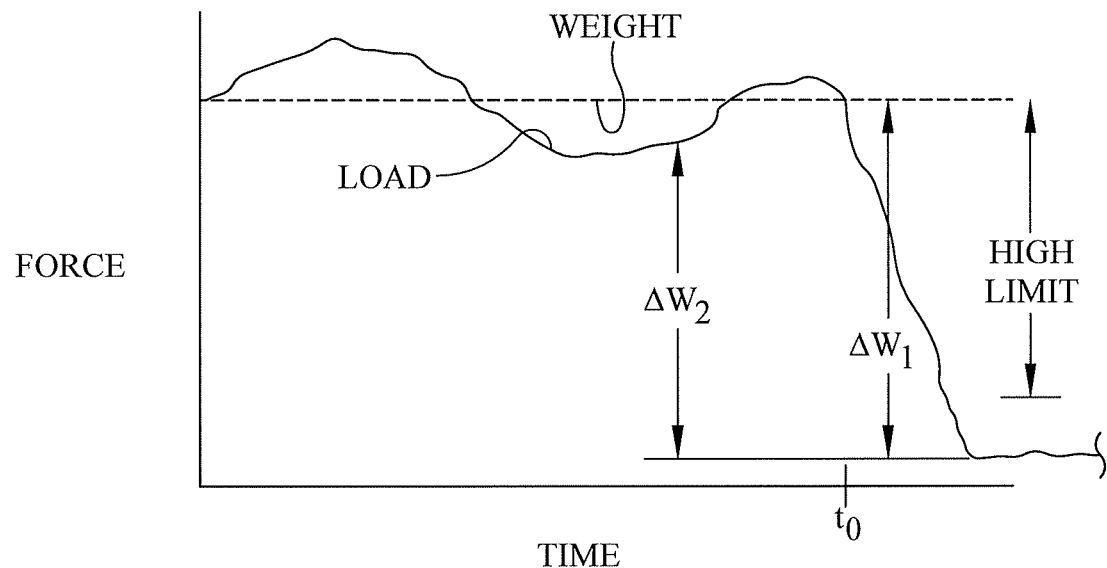
FIG. 23 is a magnification of the leftmost portion of the force vs. time graph of FIG. 4 showing two ways that can be used to determine whether all or substantially all of the patient's weight has been removed from the bed in the embodiment of FIG. 22.

At block 302, at least two ways can be used to determine whether all or substantially all of the patient's weight has been substantially removed from the bed. Referring additionally to FIG. 23, which is a magnification of the leftmost portion of FIG. 4, one way is to calculate the difference $\Delta W_1$ between the weight measure recorded in memory and the load measure after $t_0$. As already noted options for the weight measure include a discrete weight measurement carried out by a weight measuring system of the occupant support, a weight measure based on a historical record of patient weight as determined by a weight measuring system of the occupant support, and a value of the patient's weight determined from an off-board source not associated with the occupant support. Another way is to calculate the difference $\Delta W_2$ between the value of the load measure after a large change and its value prior to $t_0$, in which case the load measure at a point in time prior to $t_0$ can be considered to be the weight measure (and may be referred to as a substitute weight measure to distinguish it from the above described weight measures, which do not require recognition of a large change in the load cell readings). A value of $\Delta W_1$ or $\Delta W_2$ greater than a high limit indicates removal of all or substantially all of the patient's weight from the bed.

Figure 24:
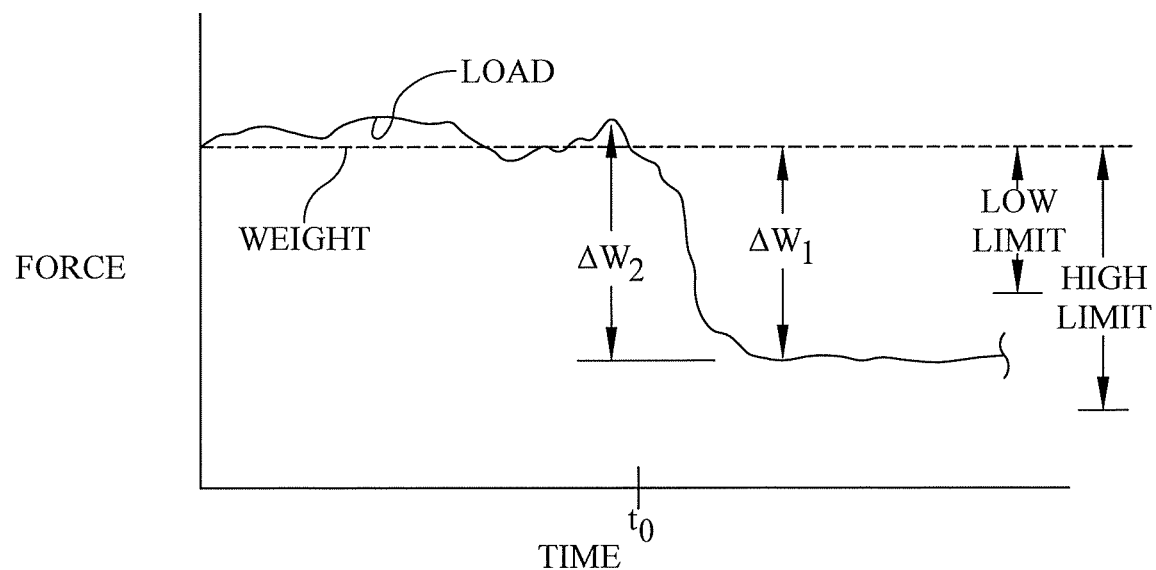
FIG. 24 is a magnification of the leftmost portion of the force vs. time graph of FIG. 5 showing how the methods illustrated in FIG. 23 can be used to determine whether less than all (but other than none) of the patient's weight has been removed from the bed.

FIG. 24, which is a magnification of the leftmost portion of FIG. 5, shows that the methods just described in connection with FIG. 23 can also be used to determine whether less than all (but other than none) of the patient's weight has been removed from the bed. A value of $\Delta W_1$ or $\Delta W_2$ greater than a low limit but less than the high limit of FIG. 23 indicates removal of less than all (but other than none) of the patient's weight from the bed.

Figure 25:
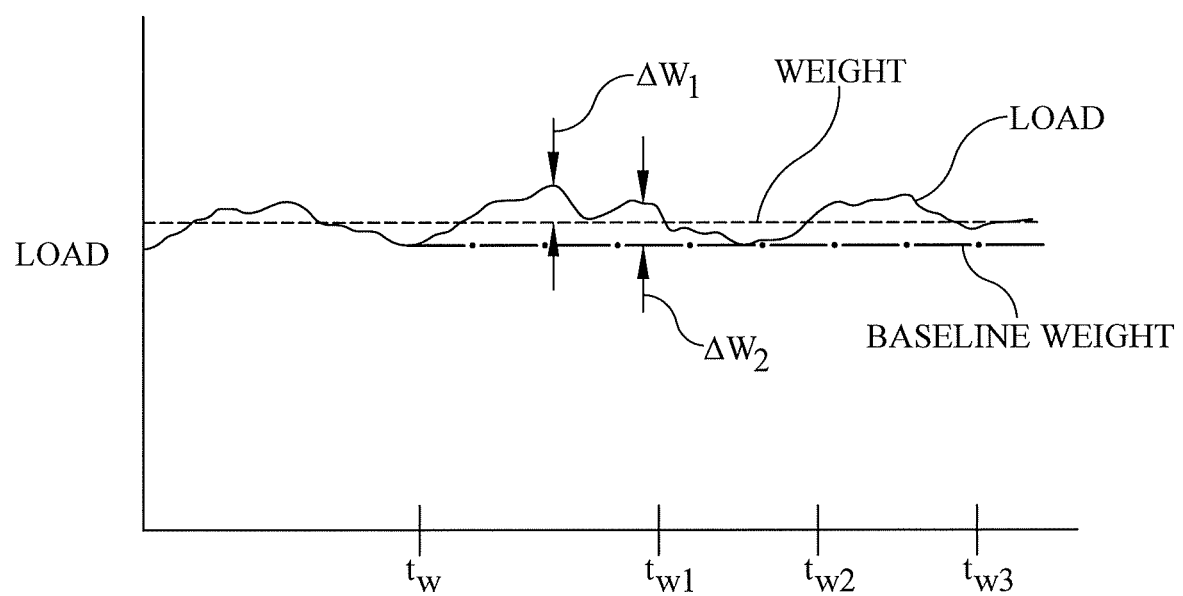
FIG. 25 is a graph similar to that of FIGS. 23-24 showing a method for determining if none or essentially none of the patient's weight has been removed from the bed.

FIG. 25 shows similar methods for determining if none or essentially none of the patient's weight was removed from the bed. In one method $\Delta W_1$ is the difference between the weight measure recorded in memory (dashed line) and the load measure (solid line). If the difference remains approximately constant over time it can be concluded that none or essentially none of the patient's weight was removed from the bed. In a similar method $\Delta W_2$ is the difference between a baseline weight measure, which is the value of the load measure at a selected time $t_w$, (dash-dot line) and the ongoing load measure (solid line). If the difference remains approximately constant over time it can be concluded that none or essentially none of the patient's weight was removed from the bed. The calculation of $\Delta W_1$ or $\Delta W_2$ is periodically repeated at times $t_{w1}$, $t_{w2}$, etc.

Figure 26:
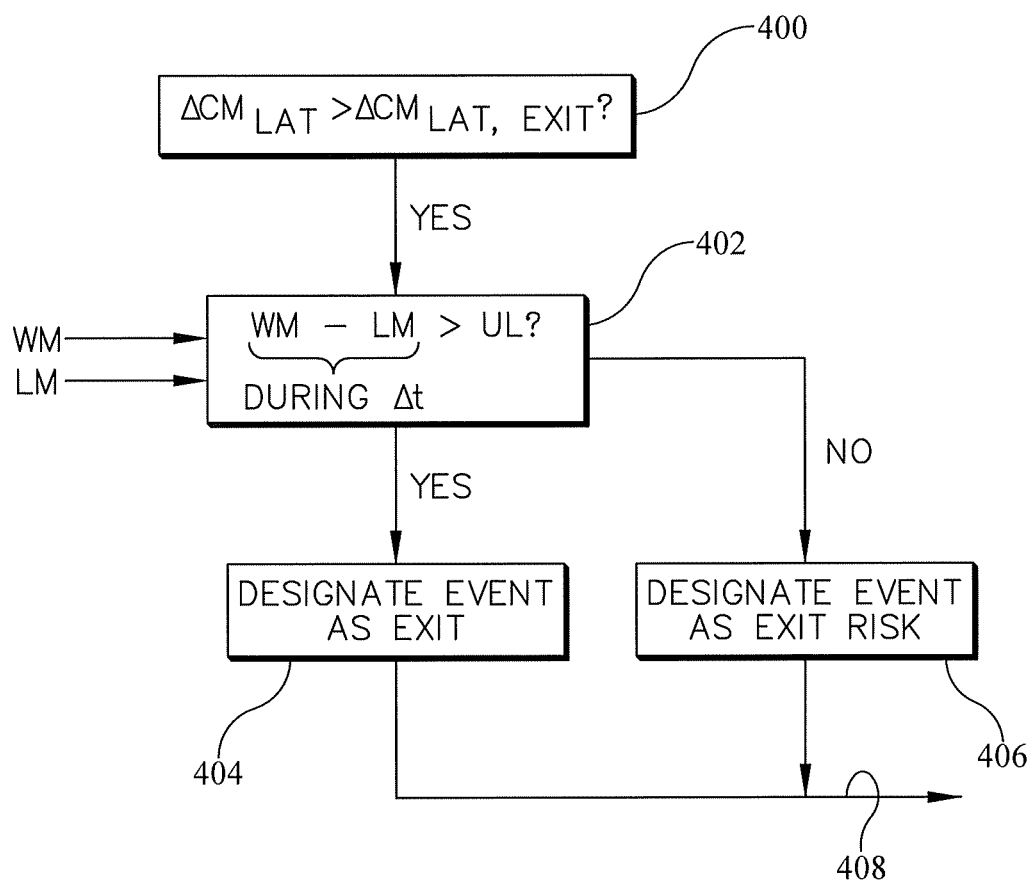
FIG. 26 is a block diagram showing an embodiment of the method which assesses whether the patient is preparing to exit the bed or has already done so.
Figure 27:
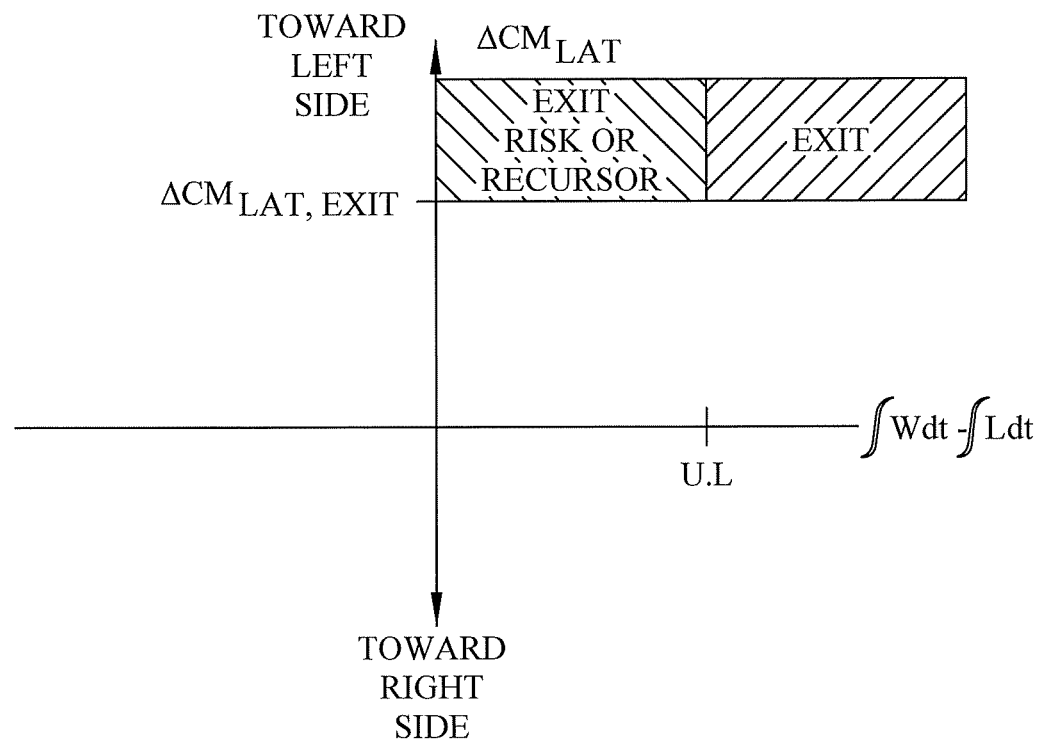
FIG. 27 is a chart similar to that of FIGS. 8, 19 and 21 depicting the logic of FIG. 26 in a more graphical form for the specific case in which a measure of the patient's weight and a measure of the load conveyed through the load cells of FIG. 3 are both represented by integrals of force over an interval of time and in which the event under consideration qualifies as an exit event (positive crosshatching) or a precursor to exit or exit risk event (negative ceosshatching).
Figure 28:
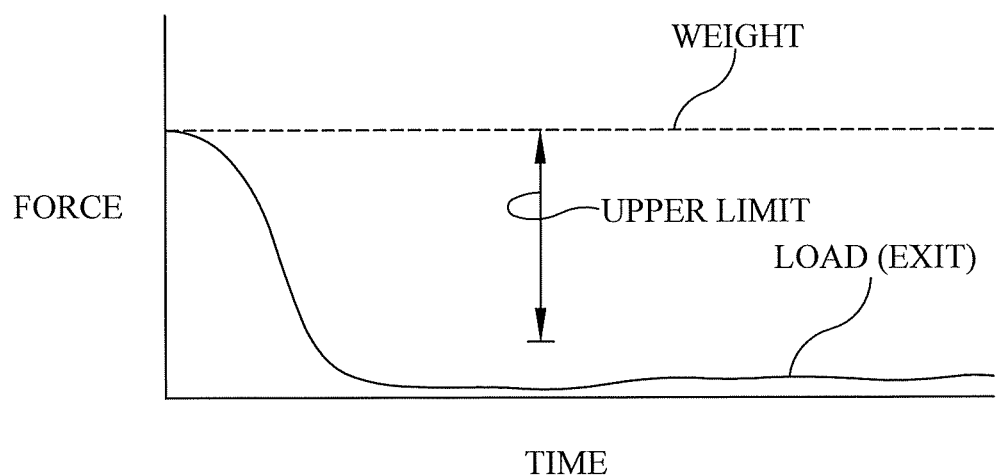
FIG. 28 is a graph of force vs. time showing patient weight (dashed line) and also showing load conveyed through the load cells of FIG. 3 for an event which qualifies as an exit event (solid line) or as an exit risk or exit precursor event (dash-dot line).

FIGS. 26-28 shows how the weight measure, the load measure and knowledge of a change in the location of the patient's center of mass may be used to assess whether the patient is preparing to exit the bed or has done so. At block 400 the method determines if the change of the patient's center of mass in the lateral direction $\Delta CM_{LAT}$ has changed by more than an exit amount $\Delta CM_{LAT, EXIT}$. The value of $\Delta CM_{LAT, EXIT}$ may be the same as the value of $\Delta CM_{LAT, MIN}$ used in other embodiments of the method, for example the embodiments of FIGS. 7, 9-18, 20, and 22, or may be different. For example a relatively smaller amount of lateral displacement might be sufficient to suggest a lateral repositioning of the patient, whereas a relatively larger amount of lateral displacement might be used to suggest that the patient has exited the bed or is preparing to do so, in which case $\Delta CM_{LAT, EXIT}$ would be larger than $\Delta CM_{LAT, MIN}$.

If the test at block 400 is satisfied the method proceeds to block 402 where it subtracts the value of the load measure LM over interval Δt from the value of the weight measure WM over interval Δt and determines if the load measure deviates from the weight measure by more than an upper limit UL. If so, as shown in FIG. 28. it is concluded that the patient has exited the bed, and the method proceeds to block 404 where it designates the event as an exit event. If not, it is concluded that the patient's weight is still on the bed. However because the patient has moved laterally far enough to suggest that he is near the laterally left or right side of the bed, the method proceeds to block 406 where it designates the event as an exit risk event or as an exit precursor. The choice of whether to designate the event as an exit risk event or as an exit precursor event may depend on whether or not the patient is authorized to exit the bed without a caregiver being present. Path 408 shows the designation being conveyed to a destination such as display 114 or a database. FIG. 27 shows the logic of FIG. 26 in a chart similar to that of FIGS. 8, 19 and 21.

As with other embodiments of the method, additional or auxiliary criteria may be used to help determine if an event is considered to be an exit event or an exit risk event. For example the lateral position change test of block 400 may be AND'd with a test of the change in the patient's longitudinal position on the bed, for example $\Delta CM_{LONG} > \Delta CM_{LONG, EXIT}$. $\Delta CM_{LONG, EXIT}$ may be the same as $\Delta CM_{LONG, MIN}$ used in other embodiments, or may be different. For example, because the patient is most likely to exit the bed at the longitudinal location of a siderail, the longitudinal change in the location of the patient's CM may be tested against the longitudinal change necessary to bring the patient into longitudinal alignment with one of the siderails.

Another possible auxiliary test is to determine if a siderail is stowed and if so whether it was placed in the stowed position recently, e.g. no longer ago than a time interval $\Delta t_{STOW}$. This is because a stowed siderail is more likely to be consistent with an attempted or actual exit than is a deployed siderail, especially if the stowage occurred shortly before the change of position of the patient's center of mass.

Yet another test applicable to the possibility of an exit event is the temporal test of block 304 of FIG. 22. A "NO" result of the test of block 304 of FIG. 22 (in conjunction with the "substantially all" result of block 302) is suggestive of an actual bed exit.

Figure 29:
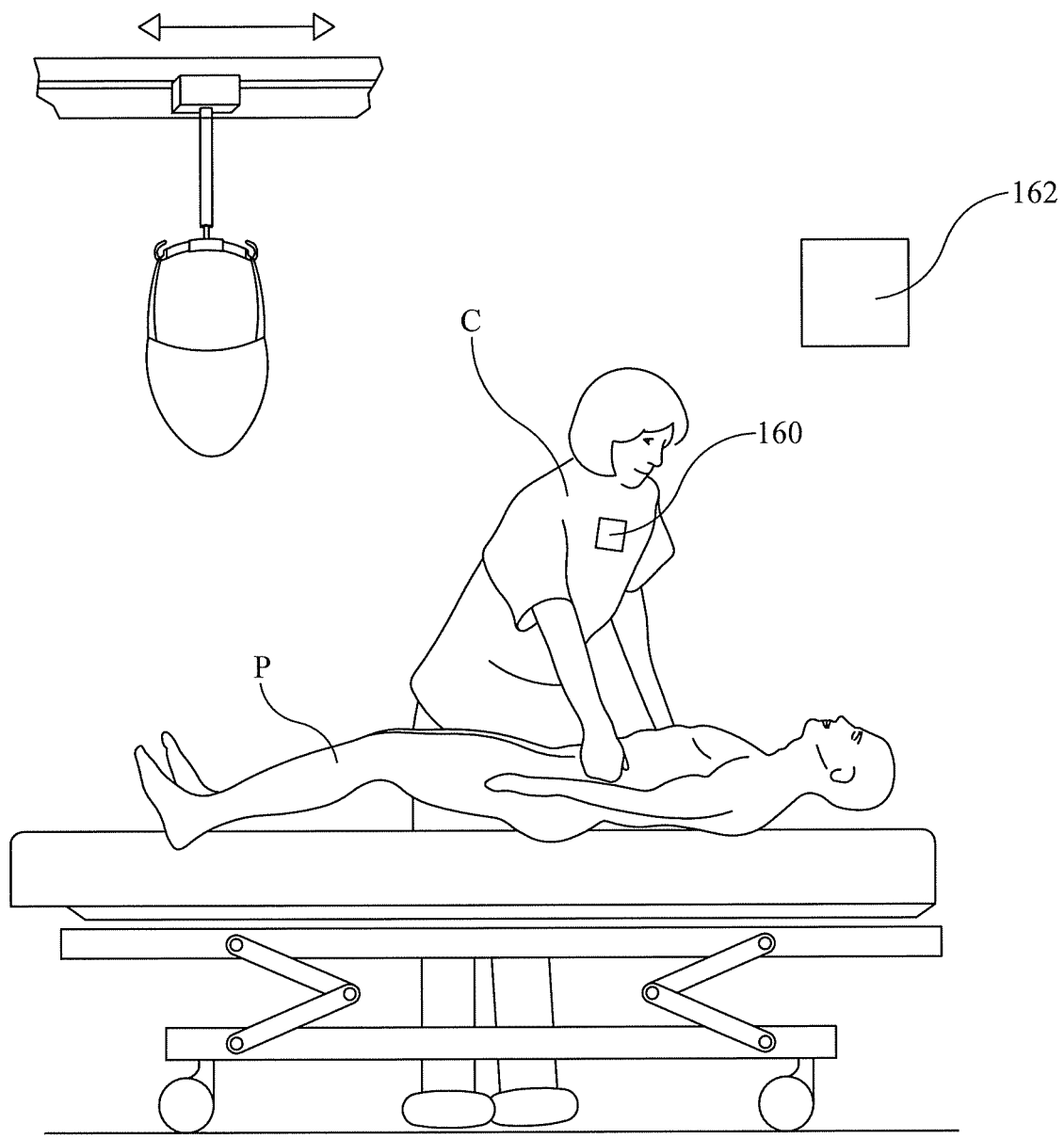
FIG. 29 is an illustration showing a patient being attended to by a caregiver wearing an RFID badge and also showing a lift system.

FIG. 29 shows a caregiver C attending to a patient P in a hospital or other care facility. The facility may have a protocol directing that all patient repositioning events be carried out with lift assistance equipment, or may have a protocol directing use of such equipment under certain circumstances or for specific patients. The caregiver is wearing an RFID badge 160. The illustration also shows a lift system comprised of a hoist 50, tether 52, slingbar 54 and sling 60. An RFID reader 162 interrogates RFID badge 160 to learn the caregiver's identity and to establish that the identified caregiver is present at the bed of patient P.

If the caregiver repositions the patient, the method as already described can determine whether or not the repositioning was carried out according to the facility repositioning protocol. The information from the RFID interrogation enables the lift event, compliant or not, to be attributed to that specific caregiver. As noted above that information can be used for staff evaluations and for justifying favorable insurance premiums.

Referring again to FIG. 3 an apparatus for distinguishing between compliant and other than compliant repositioning of an occupant of an occupant support includes processor 150 which, upon executing instructions 154, distinguishes between compliant and other than compliant repositioning of the occupant as a function of a weight measure, a load measure, and a change in the occupant's center of mass relative to the occupant support.

The act of distinguishing between compliant and other than compliant repositioning events may also be a function of an auxiliary criterion such as the criteria disclosed in connection with the above described method. The auxiliary criteria may be related to a state of the occupant support. For example if the occupant support is a bed, the auxiliary criteria may relate to deck profile, frame elevation, siderail position, frame inclination, and mattress firmness. The auxiliary criterion may also be related to a caregiver action such as effecting an adjustment to an adjustable system of the bed or commanding such an adjustment. The auxiliary criterion may be additionally or alternatively related to use of a particular user interface, such as an outwardly facing interface rather than an inwardly facing interface.

The apparatus is also adapted to recognize patient egress from the occupant support and precursors to patient egress as disclosed in connection with the above described method. The apparatus may be adapted to recognize egress and precursors to egress as a function of changes in the patient's position on the bed. The apparatus may be also adapted to recognize egress and precursors to egress as a function of an auxiliary criterion.

Figure 30:
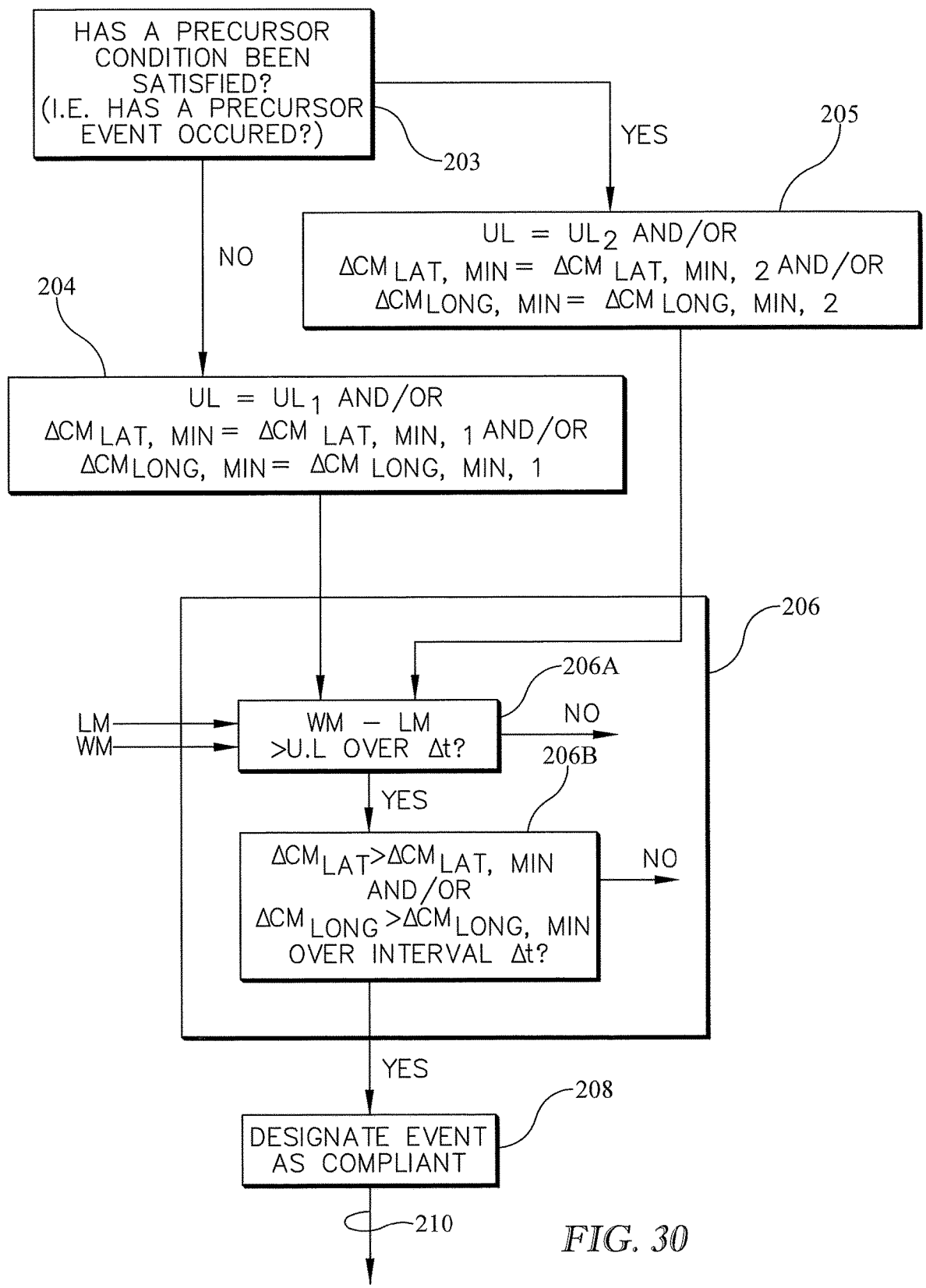
FIG. 30 is a block diagram similar to that of FIG. 9 but which includes a precursor event test which renders the subsequent tests in the diagram less likely to designate an event under consideration as a compliant event.

FIG. 30 shows an embodiment of the method similar to that of FIG. 9. In comparison to FIG. 9, FIG. 30 includes a precursor event test at block 203, but does not include the auxiliary criterion test from block 206C of FIG. 9.

At block 203 the method determines if a precursor condition has been satisfied, i.e. determines if a precursor event has occurred. A precursor event is one that would normally preceed a noncompliant repositioning event. Examples include the auxiliary criteria described earlier, such as those of FIGS. 11-17. If not, the method proceeds to block 204 where it sets at least one of UL, $\Delta CM_{LAT, MIN}$ and $\Delta CM_{LONG, MIN}$ equal to values of $UL_1$, $\Delta CM_{LAT, MIN, 1}$ and $\Delta CM_{LONG, MIN, 1}$ respectively. The method then advances to blocks 206A, 206B and 208 where it carries out the operations described previously in connection with FIG. 7.

If, at block 203, the method determines that the precursor condition has not been satisfied, i.e. that a precursor event has not occurred, the method proceeds to block 205 where it sets at least one of UL, $\Delta CM_{LAT, MIN}$ and $\Delta CM_{LONG, MIN}$ to values of $UL_2$, $\Delta CM_{LAT, MIN, 2}$ and $\Delta CM_{LONG, MIN, 2}$ respectively. The method then advances to blocks 206A, 206B and 208 where it carries out the operations described previously in connection with FIG. 7. The values of $UL_1$, $\Delta CM_{LAT, MIN, 1}$, $\Delta CM_{LONG, MIN, 1}$, $UL_2$, $\Delta CM_{LAT, MIN, 2}$, and $\Delta CM_{LONG, MIN, 2}$ are chosen so that the tests at blocks 206A and 206B will more sensitive with the 2-subscript values than with the 1-subscript values. More sensitive means more likely to follow the "NO" paths from blocks 206A and 206B and less likely to arrive at block 208. Use of the −2 subscript values reflects the fact that satisfaction of the precursor condition presages a possible noncompliant event.

Figure 31:
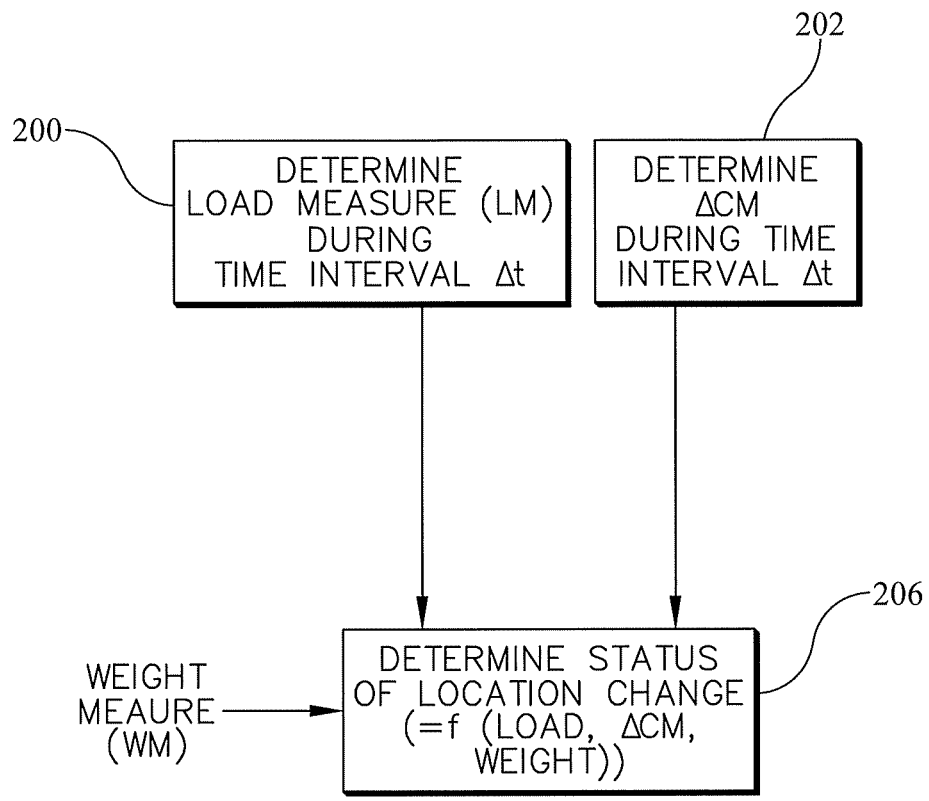
FIG. 31 is a block diagram similar to that of FIG. 6 in which the method determines the status, with respect to a protocol, of a change of the patient's location as a function of the load measure, the change of location, and a measure of the patient's weight.

FIG. 31 shows an embodiment of the method similar to that of FIG. 6. Blocks 200 and 202 are the same as the like numbered blocks of FIG. 6. At block 206 the method determines the status of the change of location with respect to the protocol as a function of the load measure, the change of location, and a measure of the patient's weight.

Figure 32:
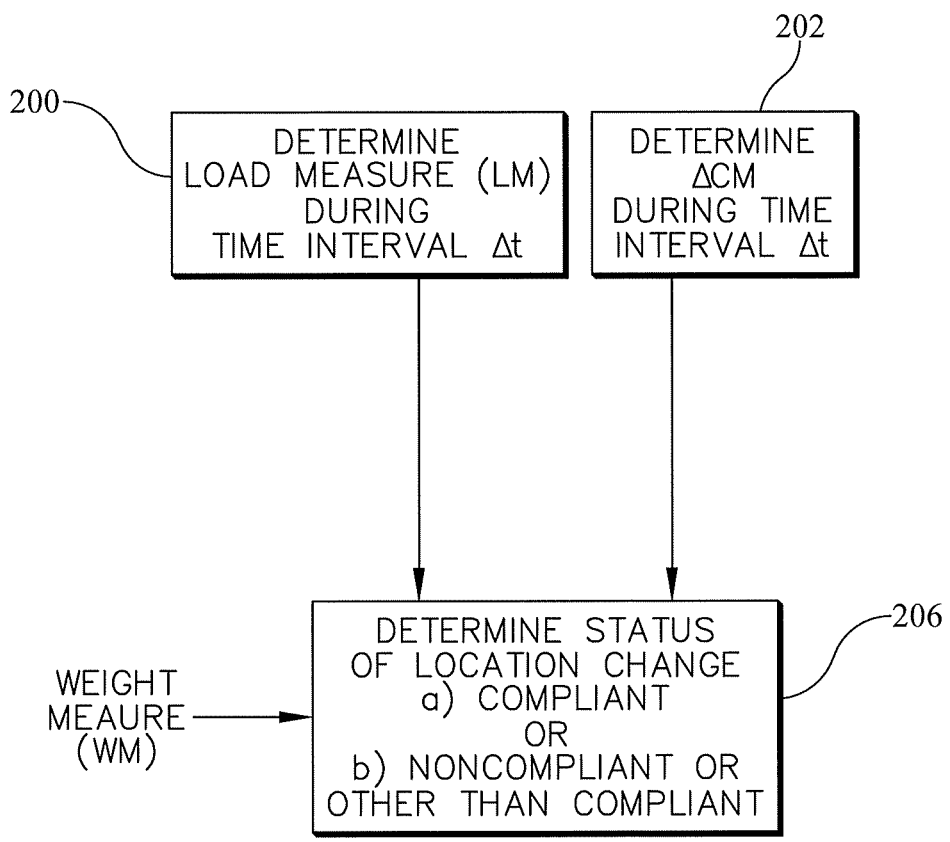
FIG. 32 is a block diagram elaborating on the method of FIG. 31.

FIG. 32 elaborates on the method of FIG. 31. The step of determining the status of the change of location with respect to the protocol at block 206 comprises one or both of a)

determining that the change of location is compliant with the protocol, and b) determining that the change of location is one of noncompliant or other than compliant.

Figure 33:
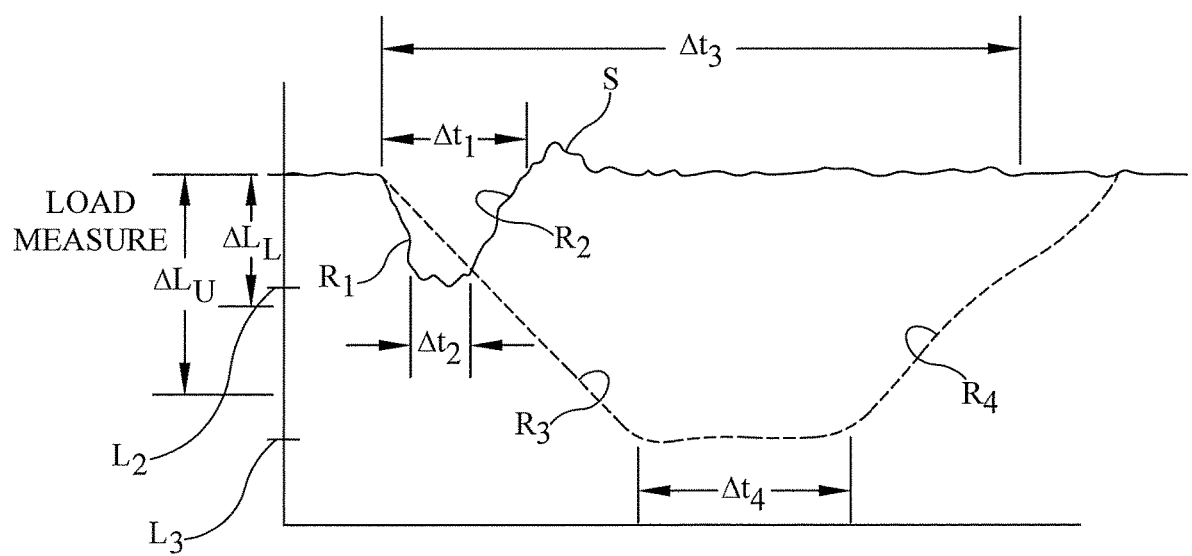
FIG. 33 is a graph illustrating use of a load measure and its temporal profile to distinguish between a compliant repositioning and a noncompliant or other than compliant repositioning.
Figure 34:
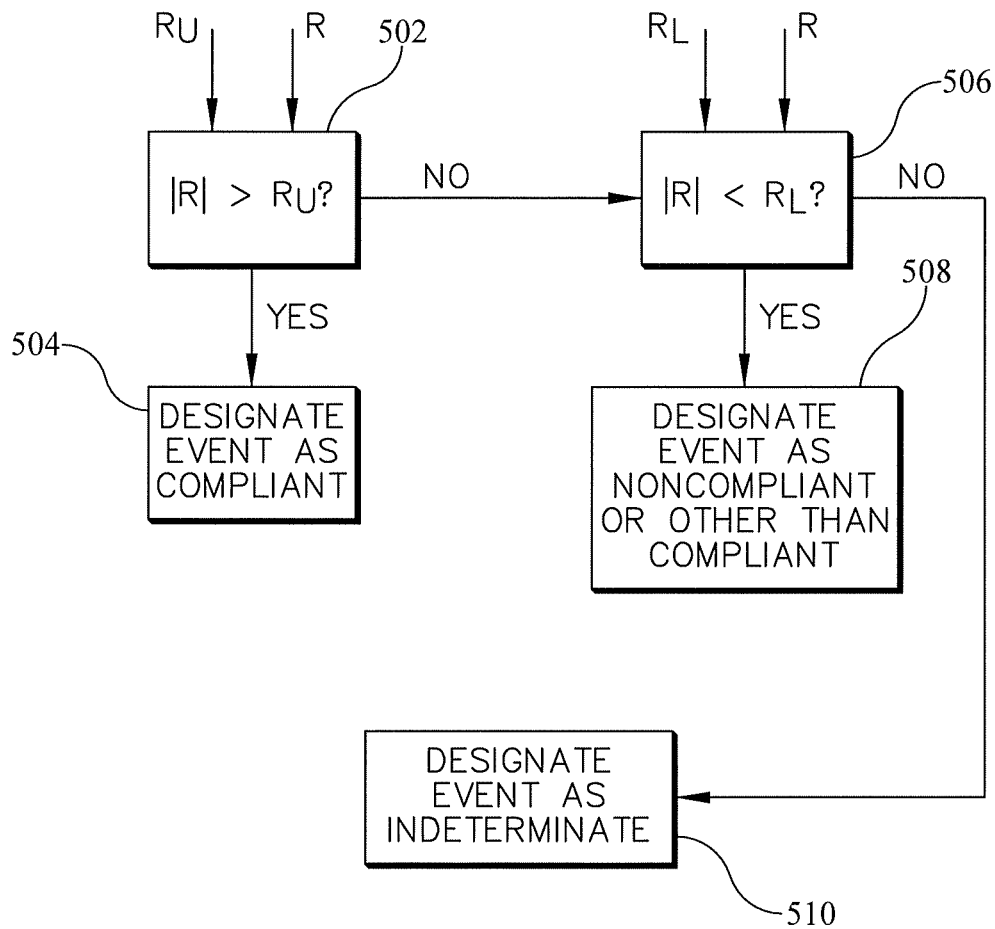
FIGS. 34-35 are block diagrams of the method of using a load measure and its temporal profile to distinguish between a compliant repositioning and a noncompliant or other than compliant repositioning.
Figure 35:
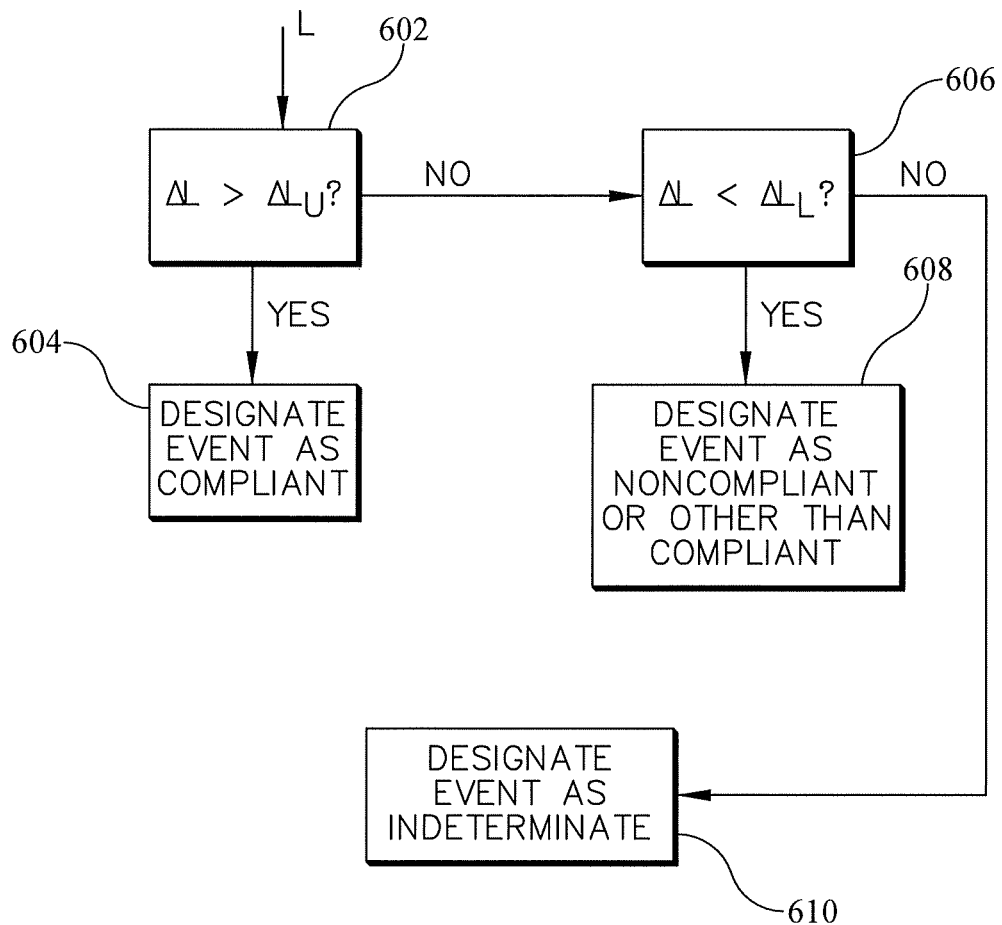

FIGS. 33-35 show an embodiment in which the load measure and its temporal profile are used to distinguish between a noncompliant repositioning (FIG. 33, solid line) and a compliant repositioning carried out with lift equipment (FIG. 33 dashed line). If a caregiver manually repositions a patient on a bed, the caregiver is likely to do so by applying an upward force on the patient, moving the patient horizontally across the bed while continuing to apply the upward force, and then discontinuing application of the upward force. Both the application and deapplication of the upward force are likely to be abrupt as indicated by high rates of change $R_1$, $R_2$ of the load versus time graph. Moreover, a large portion of the patient's weight will remain on the bed as indicated by the relatively small change in load from $L_1$ to $L_2$ detected by the load cells. The entire event, as well as the time interval during which the load is at or near its minimum, will be short (time intervals $\Delta t_1$, $\Delta t_2$). In addition the caregiver may discontinue force application so abruptly that he essentially drops the patient back onto the bed rather than lowering the patient gradually. This is indicated by the load temporarily exceeding $L_1$ at spike S.

By contrast, a compliant lift assisted repositioning (dashed line) is more likely to exhibit a more gradual removal and re-application of the patient's weight to the bed, and hence slower rates $R_3$, $R_4$ detected by the load cells. The change in load indicated by the load cells will be relatively large ($L_1$ to $L_3$). $L_3$ may be zero or substantially zero. In some cases $L_3$ may deviate noticeably from zero, for example if the caregiver uses the lift to lift the patient a small enough distance that the patient's feet remain in contact with the mattress during the repositioning of the patient. The entire event, as well as the time interval during which the load is at or near its minimum, will be relatively long (time intervals $\Delta t_3$, $\Delta t_4$). The de-application of force is likely to be more controlled than in the case of a manual repositioning. Hence the absence of a spike in the dashed line graph when it returns to value $L_1$.

FIGS. 34 and 35 show the foregoing in block diagram form. Referring first to FIG. 34, block 502 tests whether the absolute value of the rate of change of load determined from load cell readings R exceeds an upper limit $R_U$. If so the method proceeds to block 504 where it designates the event under consideration as compliant. If not the method proceeds to block 506 where it tests whether the absolute value of rate R is less than a lower limit $R_L$. If so the method proceeds to block 508 where it designates the event as noncompliant or other than compliant. If not the method proceeds to block 510 where it designates the event as indeterminate (too fast to be compliant; too slow to be noncompliant or other than compliant). Alternatively the method could test rate R against a single limit $R_{LIM}$ and designate the event compliant if R exceeds $R_{LIM}$ and as noncompliant or other than compliant if R does not exceed $R_{LIM}$.

Referring now to FIG. 35, block 602 tests whether the difference in load magnitude determined from load cell readings $\Delta L$ exceeds an upper limit $\Delta L_U$. If so the method proceeds to block 604 where it designates the event under consideration as compliant. If not the method proceeds to block 606 where it tests whether $\Delta L$ is less than a lower limit $\Delta L_L$. If so the method proceeds to block 608 where it designates the event as noncompliant or other than compliant. If not the method proceeds to block 610 where it designates the event as indeterminate (too much load change to be compliant; too little load change to be noncompliant or other than compliant). Alternatively the method could test against a single limit $\Delta L_{LIM}$ and designate the event compliant if $\Delta L$ exceeds $\Delta L_{LIM}$ and as noncompliant or other than compliant if $\Delta L$ does not exceed $\Delta L_{LIM}$.

In other embodiments the rate of change test of FIG. 34 and the load magnitude test of FIG. 35 can both be taken into account. For example the criterion for distinguishing between a compliant repositioning and a noncompliant or other than compliant repositioning could be based on the Boolean AND or OR of the rate and magnitude tests.

Although this disclosure refers to specific embodiments, it will be understood by those skilled in the art that various changes in form and detail may be made without departing from the subject matter set forth in the accompanying claims.

I claim:

1. A method for assessing compliance with a protocol requiring or advising the use of lift assist equipment for repositioning an occupant of an occupant support, the method comprising:
   determining a measure of load borne by the occupant support over an interval of time;
   using the lift assist equipment to raise the occupant upwardly relative to the occupant support and then lowering the occupant back onto the occupant support after moving the occupant relative to the occupant support while the occupant is raised;
   determining how much the location of the occupant's center of mass relative to the occupant support has changed during the interval of time; and
   assessing compliance with the protocol as a function of the load measure, the change of location, and a measure of the occupant's weight, wherein compliance with the protocol is detected (i) based on the load measure being reduced by a threshold amount as a result of the lift assist equipment being used to raise the occupant upwardly relative to the occupant support and (ii) based on a comparison of the load measure with the measure of the occupant's weight to arrive separately and additionally at a determination of a compliance of the change of location.

2. The method of claim 1 wherein:
   the measure of load exhibits a temporal load profile;
   the measure of occupant weight exhibits a temporal weight profile; and
   the step of assessing compliance accounts for the load profile and the weight profile.

3. The method of claim 1 wherein:
   the measure of load is the integral of load borne by the occupant support over the interval of time; and
   the measure of weight is the integral of occupant weight over the interval of time or a surrogate of the integral of occupant weight over the interval of time.

4. The method of claim 3 wherein if the load measure deviates from the weight measure by less than the upper limit, designating the change of location to be a noncompliant event or an other than compliant event.

5. The method of claim 4 wherein designating the change of location to be a noncompliant event or an other than compliant event is further conditioned on the load measure deviating from the weight measure by more than a lower limit which is less than the upper limit.

6. The method of claim 5 wherein if the load measure deviates from the weight measure by less than the lower limit, designating the change of location to be an autonomous repositioning of the occupant.

7. The method of claim 3 wherein the surrogate is based on a discrete weight measurement carried out by a weight measuring system of the occupant support.

8. The method of claim 3 wherein the surrogate is based on a historical record of occupant weight as determined by a weight measuring system of the occupant support.

9. The method of claim 3 wherein the surrogate is based on a value of the occupant's weight determined from a source not associated with the occupant support.

10. The method of claim 1 wherein the occupant support includes a head end, a foot end longitudinally spaced from the head end, a left side and a right lateral side laterally spaced from the left side, and the method comprises designating the change of location to be a compliant event if:
   a) the load measure indicates that all of the occupant's weight was removed from the bed and subsequently reapplied to the bed within a time period less than an exit time threshold, and
   b) the location changed in one or both of A) the lateral direction by a minimum lateral amount and B) the longitudinal direction by more than a minimum longitudinal amount.

11. The method of claim 1 wherein the occupant support includes a head end, a foot end longitudinally spaced from the head end, a left side and a right lateral side laterally spaced from the left side, and the method comprises designating the change of location to be an autonomous repositioning of the occupant if:
   a) the load measure indicates nonremoval of the occupant's weight from the bed, and
   b) the location changed in one or both of the lateral direction by a minimum lateral amount and the longitudinal direction by more than a minimum longitudinal amount.

12. The method of claim 1 wherein the step of assessing compliance takes at least one auxiliary criterion into account.

13. The method of claim 1 wherein the protocol always requires use of the lift assist equipment.

14. The method of claim 1 wherein the occupant support includes a head end, a foot end longitudinally spaced from the head end, a left side and a right lateral side laterally spaced from the left side, and the method comprises designating the change of location to be an exit event if:
   a) the location changed in a direction having a lateral component exceeding an exit lateral amount, and
   b) the load measure deviates from the weight measure by more than an upper limit.

15. The method of claim 1 wherein the occupant support includes a head end, a foot end longitudinally spaced from the head end, a left side and a right lateral side laterally spaced from the left side, and the method comprises designating the change of location to be an exit risk event or exit precursor event if:
   a) the location changed in a direction having a lateral component exceeding a minimum lateral amount, and
   b) the load measure deviates from the weight measure by less than an upper limit.

16. The method of claim 1 comprising determining if a caregiver is present, determining the identity of the present caregiver, and attributing compliance and/or lack thereof to the identified caregiver.

17. A method for assessing compliance with a protocol requiring or advising the use of lift assist equipment for repositioning an occupant of an occupant support, the method comprising:
   determining a measure of load borne by the occupant support over an interval of time;
   using the lift assist equipment to raise the occupant upwardly relative to the occupant support and then lowering the occupant back onto the occupant support after moving the occupant relative to the occupant support while the occupant is raised;
   determining how much the location of the occupant's center of mass relative to the occupant support has changed during the interval of time; and
   assessing compliance with the protocol as a function of the load measure, the change of location, and a measure of the occupant's weight;
   wherein the measure of load is the integral of load borne by the occupant support over the interval of time;
   wherein the measure of weight is the integral of occupant weight over the interval of time or a surrogate of the integral of occupant weight over the interval of time;
   wherein the occupant support includes a head end, a foot end longitudinally spaced from the head end, a left side and a right lateral side laterally spaced from the left side, and the method comprises designating the change of location to be a compliant event if:
   a) the load measure deviates from the weight measure by more than an upper limit, and
   b) the location changed in the longitudinal direction by more than a minimum longitudinal amount and/or changed in the lateral direction by more than a minimum lateral amount.

18. The method of claim 17 wherein designating the change of location as a compliant event is further conditioned on satisfaction of at least one auxiliary criterion.

19. The method of claim 18 wherein the bed includes an adjustable feature and the auxiliary criterion to be satisfied is actual or commanded adjustment of the adjustable feature prior to a candidate event.

20. The method of claim 19 wherein the bed includes an outwardly facing user interface and the criterion to be satisfied further includes use of the user interface to effect the actual adjustment or command the adjustment of the adjustable features.

21. The method of claim 18 wherein the bed includes an outwardly facing user interface and the auxiliary criterion to be satisfied is use of the outwardly facing user interface prior to a candidate event.

22. The method of claim 21, wherein the bed includes an adjustable feature which is adjustable by use of the outwardly facing user interface, and the auxiliary criterion to be satisfied further includes use of the user interface to effect an actual or commanded adjustment of the adjustable feature.

23. The method of claim 18 wherein the bed includes an adjustable feature comprising at least one of:
   a siderail which is positionable at at least a fully deployed position and a fully stowed position; and
   a frame which is at least one of profile adjustable, and elevation adjustable;
   and the auxiliary criterion to be satisfied is actual or commanded adjustment, prior to a candidate event, of one or more of: a) siderail position, b) frame profile and c) frame elevation.

24. The method of claim 23 wherein the auxiliary criterion to be satisfied is at least one of:
   the siderail having been lowered;
   a torso section of a deck section of the frame having been changed toward a horizontal orientation, and
   elevation of the frame having been increased from a lower elevation to a higher elevation.

25. The method of claim 18 wherein the bed includes an adjustable feature comprising at least one of:
 a frame which is orientational adjustable; and
 a mattress which is condition adjustable;
 and the auxiliary criterion to be satisfied is absence of an actual or commanded adjustment, prior to a candidate event, of one or more of a) frame orientation and b) mattress condition.

26. The method of claim 25 wherein the auxiliary criterion to be satisfied is at least one of:
 absence of a decrease in orientation angle of the frame, and
 absence of the mattress having been placed in a condition more favorable than not for manual repositioning.

27. The method of claim 26 wherein the condition which is not more favorable for manual repositioning is a state of less firmness of the mattress and the condition which is more favorable for manual repositioning is a state of more firmness of the mattress.

28. The method of claim 26 wherein the mattress is selectively pressurizable, the not more favorable condition is a state of lower internal bladder pressure and the more favorable condition is a state of higher internal bladder pressure.

29. A apparatus for distinguishing between compliant and other than compliant repositioning of an occupant of an occupant support using lift assist equipment, the apparatus comprising:
 a processor;
 instructions which are executable by the processor and which, when executed, cause the apparatus to distinguish between compliant and other than compliant repositioning of the occupant as a function of a weight measure, a load measure, and a change of location in the occupant's center of mass relative to the occupant support, wherein compliant repositioning corresponds to use of the lift assist equipment to raise the occupant upwardly relative to the occupant support and then lowering the occupant back onto the occupant support after moving the occupant relative to the occupant support while the occupant is raised such that compliant repositioning is detected (i) based on the load measure being reduced by a threshold amount as a result of the lift assist equipment being used to raise the occupant upwardly relative to the occupant support and (ii) based on a comparison of the load measure with the weight measure to arrive separately and additionally at a determination of a compliance of the change of location.

30. The apparatus of claim 29 wherein distinguishing between compliant and other than compliant repositioning is also a function of an auxiliary criterion.

31. The apparatus of claim 30 wherein the auxiliary criterion relates to a state of the occupant support.

32. The apparatus of claim 30 wherein the auxiliary criterion relates to one or both of:
 a) an adjustment to an adjustable system of the occupant support having been effected or commanded, and
 b) use of a particular user interface.

33. The apparatus of claim 29 wherein the apparatus is also adapted to recognize noncompliant repositioning.

34. The apparatus of claim 29 wherein the apparatus is also adapted to recognize occupant egress from the occupant support and precursors to occupant egress.

35. The apparatus of claim 34 wherein recognition of egress and precursors to egress is a function of changes in the occupant's position on the bed.

36. The apparatus of claim 35 wherein the recognition of egress and precursors to egress is also a function of an auxiliary criterion.

37. A method for assessing compliance with a protocol requiring or advising the use of lift assist equipment for repositioning an occupant of an occupant support, the method comprising:
 determining a measure of load borne by the occupant support over an interval of time;
 using the lift assist equipment to raise the occupant upwardly relative to the occupant support and then lowering the occupant back onto the occupant support after moving the occupant relative to the occupant support while the occupant is raised;
 determining how much the location of the occupant's center of mass relative to the occupant support has changed during the interval of time; and
 determining the status of the change of location with respect to the protocol as a function of the load measure, the change of location, and a measure of the occupant's weight, wherein compliance with the protocol is detected (i) based on the load measure being reduced by a threshold amount as a result of the lift assist equipment being used to raise the occupant upwardly relative to the occupant support and (ii) based on a comparison of the load measure with the measure of the occupant's weight to arrive separately and additionally at a determination of a compliance of the change of location.

* * * * *